US006850801B2

(12) United States Patent
Kieval et al.

(10) Patent No.: US 6,850,801 B2
(45) Date of Patent: Feb. 1, 2005

(54) MAPPING METHODS FOR CARDIOVASCULAR REFLEX CONTROL DEVICES

(75) Inventors: Robert S. Kieval, Medina, MN (US); Bruce J. Persson, Albertville, MN (US); David J. Serdar, Shorewood, MN (US); Peter T. Keith, St. Paul, MN (US)

(73) Assignee: CVRx, Inc., Maple Grove, MN (US)

( * ) Notice: Subject to any disclaimer, the term of this patent is extended or adjusted under 35 U.S.C. 154(b) by 616 days.

(21) Appl. No.: 09/963,991

(22) Filed: Sep. 26, 2001

(65) Prior Publication Data

US 2003/0060848 A1 Mar. 27, 2003

(51) Int. Cl.⁷ .................................................. A61N 1/08
(52) U.S. Cl. .................................... 607/44; 600/485
(58) Field of Search ............................ 607/2, 3, 44, 62, 607/67, 72, 118, 46, 48; 600/377, 381, 485, 500, 505, 552–555, 547, 548

(56) References Cited

U.S. PATENT DOCUMENTS

| | | |
|---|---|---|
| 3,522,811 A | 8/1970 | Schwartz et al. |
| 3,645,267 A | 2/1972 | Hagfors |
| 3,650,277 A | 3/1972 | Sjostrand et al. |
| 3,943,936 A | 3/1976 | Rasor et al. |
| 4,014,318 A | 3/1977 | Dockum et al. |
| RE30,366 E | 8/1980 | Rasor et al. |
| 4,256,094 A | 3/1981 | Kapp et al. |
| 4,323,073 A | 4/1982 | Ferris |
| 4,331,157 A | 5/1982 | Keller, Jr. et al. |
| 4,481,953 A | 11/1984 | Gold et al. |
| 4,525,074 A | 6/1985 | Murakami |
| 4,531,943 A | 7/1985 | Van Tassel et al. |
| 4,551,862 A | 11/1985 | Haber |
| 4,586,501 A | 5/1986 | Claracq |
| 4,640,286 A | 2/1987 | Thomson |
| 4,641,664 A | 2/1987 | Botvidsson |
| 4,664,120 A | 5/1987 | Hess |
| 4,682,583 A | 7/1987 | Burton et al. |
| 4,702,254 A | 10/1987 | Zabara |
| 4,709,690 A | 12/1987 | Habor |
| 4,719,921 A | 1/1988 | Chirife |
| 4,739,762 A | 4/1988 | Palmaz |
| 4,762,130 A | 8/1988 | Fogarty et al. |
| 4,762,820 A | 8/1988 | Gavras |
| 4,770,177 A | 9/1988 | Schroeppel |

(List continued on next page.)

FOREIGN PATENT DOCUMENTS

| | | |
|---|---|---|
| WO | WO 9718856 | 5/1997 |
| WO | WO 99/26530 | 6/1999 |
| WO | WO 99/42039 | 8/1999 |
| WO | WO 99/42176 | 8/1999 |

OTHER PUBLICATIONS

U.S. patent application Ser. No. 09/964,079, filed Sep. 26, 2001 entitled "Stimulus Regimens for Cardiovascular Reflex Control" to Robert S. Kieval et al.

U.S. patent application Ser. No. 09/963,777, filed Sep. 26, 2001 entitled "Electrode Designs and Methods of Use for Cardiovascular Reflex Control Devices" to Robert S. Kieval et al.

"Cardiovascular Reflexes From Ventricular & Coronary Receptors", *Adv. Exp. Med. Biol.*, 1995, 381:157–74.

(List continued on next page.)

*Primary Examiner*—Jeffrey R. Jastrzab
*Assistant Examiner*—Frances P. Oropeza
(74) *Attorney, Agent, or Firm*—Townsend & Townsend and Crew LLP

(57) ABSTRACT

Devices, systems and methods by which the blood pressure, nervous system activity, and neurohormonal activity may be selectively and controllably reduced by activating baroreceptors. A baroreceptor activation device is positioned near a baroreceptor, preferably in the carotid sinus. A mapping method permits the baroreceptor activation device to be precisely located to maximize therapeutic efficacy.

15 Claims, 25 Drawing Sheets

U.S. PATENT DOCUMENTS

| | | |
|---|---|---|
| 4,791,931 A | 12/1988 | Slate |
| 4,800,882 A | 1/1989 | Gianturco |
| 4,803,988 A | 2/1989 | Thomson |
| 4,813,418 A | 3/1989 | Harris |
| 4,825,871 A | 5/1989 | Cansell |
| 4,828,544 A | 5/1989 | Lane et al. |
| 4,830,003 A | 5/1989 | Wolff et al. |
| 4,860,751 A | 8/1989 | Callaghan |
| 4,867,164 A | 9/1989 | Zabara |
| 4,881,939 A | 11/1989 | Newman |
| 4,886,062 A | 12/1989 | Wiktor |
| 4,887,608 A | 12/1989 | Mohl et al. |
| 4,917,092 A | 4/1990 | Todd et al. |
| 4,960,133 A | 10/1990 | Hewson |
| 4,969,458 A | 11/1990 | Wiktor |
| 5,025,807 A | 6/1991 | Zabara |
| 5,040,533 A | 8/1991 | Fearnot |
| 5,078,736 A | 1/1992 | Behl |
| 5,113,869 A | 5/1992 | Nappholz et al. |
| 5,117,826 A | 6/1992 | Bartelt et al. |
| 5,170,802 A | 12/1992 | Mehra |
| 5,181,911 A | 1/1993 | Shturman |
| 5,199,428 A | 4/1993 | Obel et al. |
| 5,215,089 A | 6/1993 | Baker, Jr. |
| 5,222,971 A | 6/1993 | Willard et al. |
| 5,224,491 A | 7/1993 | Mehra |
| 5,259,394 A | 11/1993 | Bens |
| 5,295,959 A | 3/1994 | Gurbel et al. |
| 5,299,569 A | 4/1994 | Wernicke et al. |
| 5,304,206 A | 4/1994 | Baker, Jr. et al. |
| 5,314,453 A | 5/1994 | Jeutter |
| 5,318,592 A | 6/1994 | Schaldach |
| 5,330,507 A | 7/1994 | Schwartz |
| 5,330,515 A | 7/1994 | Rutecki et al. |
| 5,351,394 A | 10/1994 | Weinberg |
| 5,411,540 A | 5/1995 | Edell et al. |
| 5,458,626 A | 10/1995 | Krause |
| 5,509,888 A | 4/1996 | Miller |
| 5,522,854 A | 6/1996 | Ideker et al. |
| 5,529,067 A | 6/1996 | Larsen et al. |
| 5,531,779 A | 7/1996 | Dahl et al. |
| 5,535,752 A | 7/1996 | Halperin et al. |
| 5,540,734 A | 7/1996 | Zabara |
| 5,540,735 A | 7/1996 | Wingrove |
| 5,545,132 A | 8/1996 | Fagan et al. |
| 5,545,202 A | 8/1996 | Dahl et al. |
| 5,571,150 A | 11/1996 | Wernicke et al. |
| 5,575,809 A | 11/1996 | Sasaki |
| 5,578,061 A | 11/1996 | Stroetmann et al. |
| 5,634,878 A | 6/1997 | Grundei et al. |
| 5,643,330 A | 7/1997 | Holsheimer et al. |
| 5,651,378 A | 7/1997 | Matheny et al. |
| 5,690,681 A | 11/1997 | Geddes et al. |
| 5,692,882 A | 12/1997 | Bozeman, Jr. et al. |
| 5,695,468 A | 12/1997 | Lafontaine et al. |
| 5,700,282 A | 12/1997 | Zabara |
| 5,707,400 A | 1/1998 | Terry, Jr. et al. |
| 5,715,837 A | 2/1998 | Chen |
| 5,725,471 A | 3/1998 | Davey et al. |
| 5,725,563 A | 3/1998 | Klotz |
| 5,727,558 A | 3/1998 | Hakki et al. |
| 5,741,316 A | 4/1998 | Chen et al. |
| 5,766,236 A | 6/1998 | Detty et al. |
| 5,800,464 A | 9/1998 | Kieval |
| 5,807,258 A | 9/1998 | Cimochowski et al. |
| 5,814,079 A | 9/1998 | Kieval |
| 5,824,021 A | 10/1998 | Rise |
| 5,861,015 A | 1/1999 | Benja-Athon |
| 5,876,422 A | 3/1999 | van Groeningen |
| 5,891,181 A | 4/1999 | Zhu |
| 5,913,876 A | 6/1999 | Taylor et al. |
| 5,916,239 A | 6/1999 | Geddes et al. |
| 5,928,272 A | 7/1999 | Adkins et al. |
| 5,967,986 A | 10/1999 | Cimochowski et al. |
| 5,967,989 A | 10/1999 | Cimochowski et al. |
| 5,987,352 A | 11/1999 | Klein et al. |
| 5,989,230 A | 11/1999 | Frassica |
| 6,006,134 A | 12/1999 | Hill et al. |
| 6,016,449 A | 1/2000 | Fischell et al. |
| 6,023,642 A | 2/2000 | Shealy et al. |
| 6,050,952 A | 4/2000 | Hakki et al. |
| 6,052,623 A | 4/2000 | Fenner et al. |
| 6,058,331 A | 5/2000 | King |
| 6,061,596 A | 5/2000 | Richmond et al. |
| 6,073,048 A | 6/2000 | Kieval et al. |
| 6,077,227 A | 6/2000 | Miesel et al. |
| 6,077,298 A | 6/2000 | Tu et al. |
| 6,161,029 A | 12/2000 | Spreigl et al. |
| 6,178,349 B1 | 1/2001 | Kieval |
| 6,231,516 B1 | 5/2001 | Keilman et al. |
| 6,292,695 B1 | 9/2001 | Webster, Jr. et al. |
| 6,438,428 B1 | 8/2002 | Axelgaard et al. |
| 6,564,101 B1 | 5/2003 | Zikria |
| 2001/0020177 A1 | 9/2001 | Gruzdowich et al. |
| 2002/0005982 A1 | 1/2002 | Borlinghaus |
| 2002/0103516 A1 | 8/2002 | Patwardhan et al. |
| 2002/0151051 A1 | 10/2002 | Li |
| 2003/0040785 A1 | 2/2003 | Maschino et al. |

OTHER PUBLICATIONS

"Non–Invasive Heat–Delivery To Arterial Stented Segments In Vivo: Effect of Heat on Intimal Hyperplasia", *JACC*, 1041–89, Feb. 2000.

"The Haemodynamic Basis of Anginal Relief Produced By Stimulation of the Carotid Sinus Nerve", *Acta Medica Academiae Scientiarum Hungaricae*, 30 (1–2), pp. 61–65, 1973.

Correspondence, *The New England of Journal of Medicine*, vol. 281, Jul. 3, 1969, No. 2.

"Carotid Sinus Stimulation For the Treatment of Angina Pectoris", *Official Journal of the Calif. Medical Assoc.*, vol. 112, No. 3, pps. 78–79, Mar. 1970.

"Circulatory Effects of Carotid Sinus Stimulation & Changes in Blood Volume Distribution in Hypertensive Man", *Acta. Physiol. Scand.*, 1981, 111:299–306, Mar. 1981.

"Surgical Treatment of Hypertension with Reference to Baropacing", *The Amer. Jour. Of Cardiology*, vol. 17, May 1966, pps. 663–667.

"Baropacing of the Carotid Sinus Nerve for Treatment of Intractable Hypertension", *Zeitschrift Für Kardiologie*, band 64, Heft 4, pps. 368–374, 1975.

"Laryngospasm Induced by a Carotid–Sinus–Nerve Stimulator", *The New England Journ. Of Med.*, No. 13, pps. 709–710, undated, admitted prior art.

"Fine Structure of Baroreceptor Terminals in the Carotid Sinus of Guinea Pigs & Mice", *Cell & Tissue Research*, 170, pps. 95–112 , 1976.

"Structure of Rat Aortic Baroreceptors & Their Relationship to Connective Tissue", *Journal of Neurocytology*, pps. 401–414, 1979.

"Baroreflex Anatomy", *Human Baroreflexes in Health & Disease*, pps. 19–30, 1992.

"Implantation of a Carotid Sinus Nerve Stimulator", *AORN Journal*, pps. 53–56, Dec. 1969.

"The Treatment of Heart Disease", *Heart Disease*, Earl N. Silber, $2^{nd}$ Edition, MacMillan Publishing Co., p. 1642, 1987.

"Stimulation of the Carotid Baroreceptors Using a Radio–Frequency Method", *Israel J. Med. Sci.*, vol. 1, No. 4, Jul. 1965, pps. 630–632.

"Studies on the Carotid Body & the Carotid Sinus Effects on the Heart by Electrical Stimulation of the Carotid Sinus Wall", *Jap. Heart J.*, vol. 13, No. 2, Mar. 1972, pps. 136–149.

"Abstracts of the $40^{th}$ Scientific Sessions", Supplement II to Circulation, vols. XXXV & XXXVI, Oct. 1967, II–253, 1 sheet.

Transvenous parasympathetic nerve stimulation in the inferior vena cava and atrioventricular conduction, *J. Cardiovasc. Electrophysiol.*, Jan. 2000, 1 page.

"New Technique for Vagal Nerve Stimulation", Journal of Neuroscience Methods, 1999, pp. 109–114.

"Clinical Experience with a Helical Bipolar Stimulating Lead", PACE, vol. 15, Part II, Oct. 1992, pp. 1545–1556.

U.S. patent application Ser. No. 09/963,777, Perrson et al., filed Sep. 26, 2001.

U.S. patent application Ser. No. 09/964,079, Kieval et al., filed Sep. 26, 2001.

Bilgutay, A.M., et al., "Baropacing, a New Concept in the Treatment of Hypertension", from Baroreceptors and Hypertension Proceedings of an International Symposium, Nov., 1965, p. 425–437.

Brattstrom, A., Influence of Continuous and Intermittent (R–Wave Triggered) Electrical Stimulation of the Carotid Sinus Nerve on the Static Characteristic of the Circularoty Regulator:, Experientia 28:414–416, 1972.

Peters et al., The Principle of Electrical Carotid Sinus Nerve Stimulation: A Nerve Pacemaker System for Angina Pectoris and Hypertension Therapy, Annals of Biomedical Engineering, 8:445–458, 1980.

Peters et al., Cardiovascular response to time delays of electrocardiogram–coupled electrical stimulation of carotid sinus nerves in dogs, Journal of the Autonomic Nervous Systems, 25:173–180, 1988.

Richter et al., The Course of Inhibition of Sympathetic Activity during Various Patterns of Carotid Sinus Nerve Stimulation, Pflugers Arch., 317:110–123, 1970.

Sedin, Gunnar, Responses of the Cardiovascular System to Carotid Sinus Nerve Stimulation, Upsala J Med Sci, 81:1–17, 1976.

Warzel et. al., Effects of carotis sinus nerve stimulation at different times in the respiratory and cardiac cycles on variability of heart rate and blood pressure of normotensive and renal hypertensive dogs, Journal of the Autonomic Nervous System, 26:121–127, 1989.

Warzel et. al., The Effect of Time of Electrical Stimulation of the Carotid Sinus on the Amount of Reduction in Arterial Pressure, Pflugers Arch., 337:39–44, 1972.

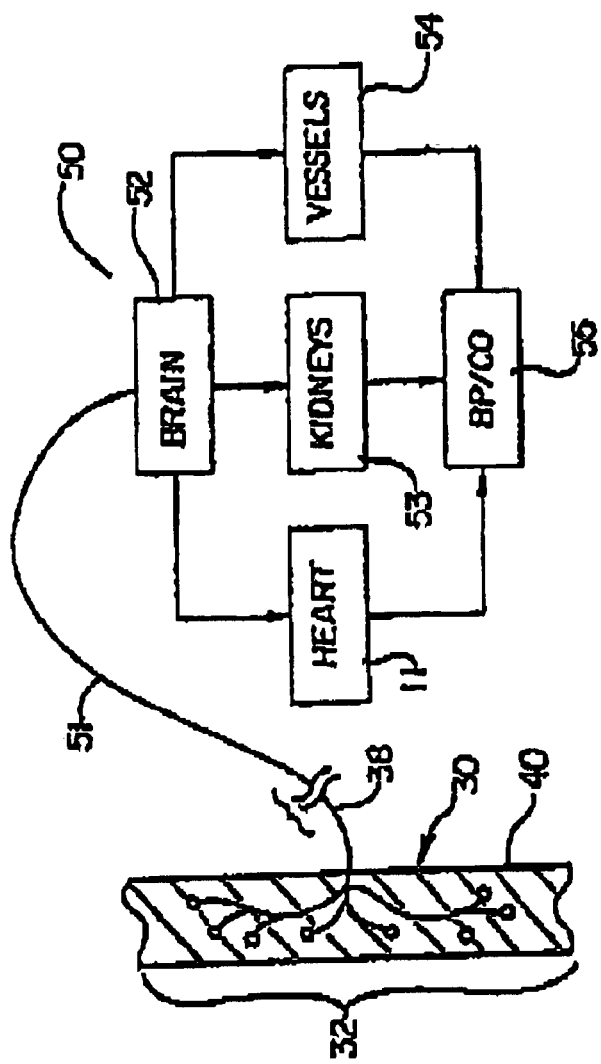
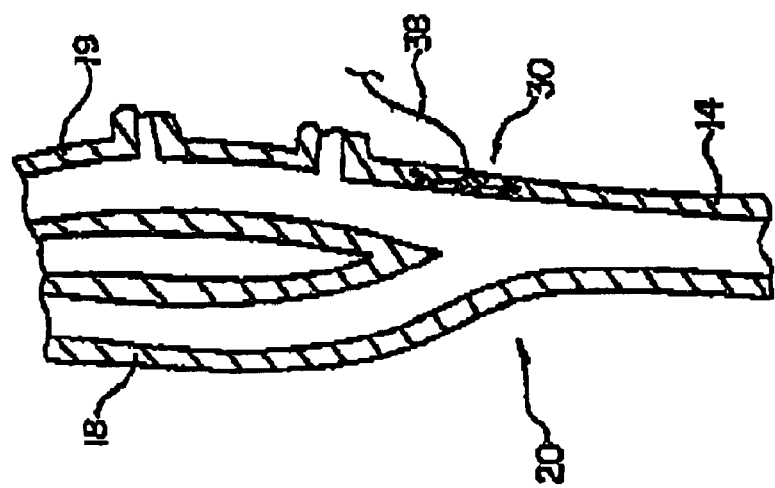

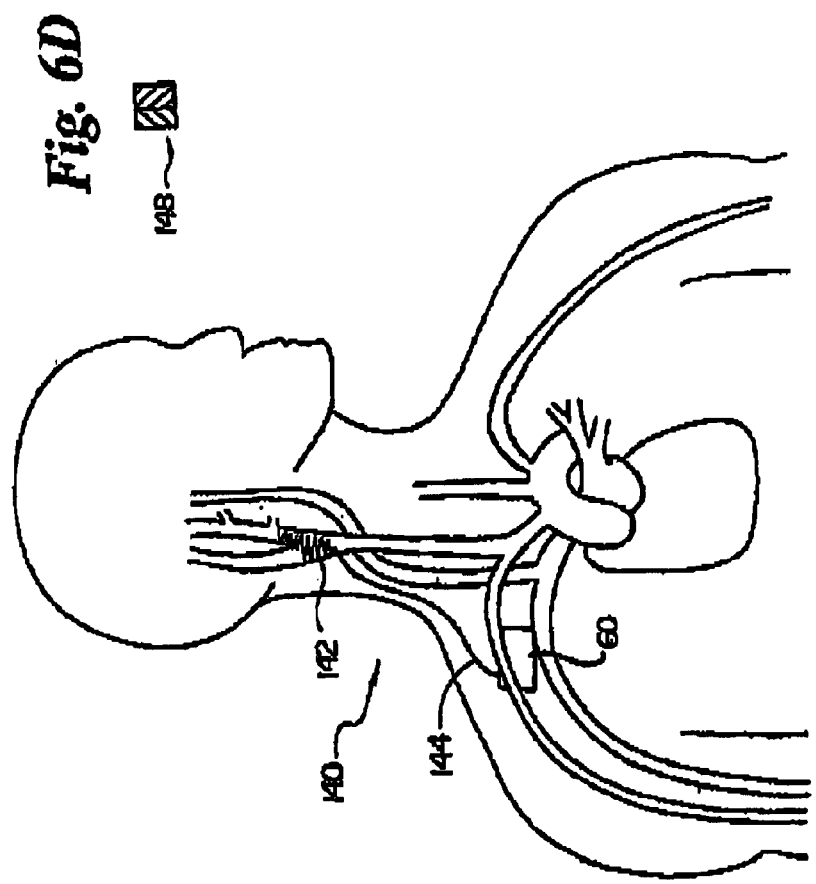
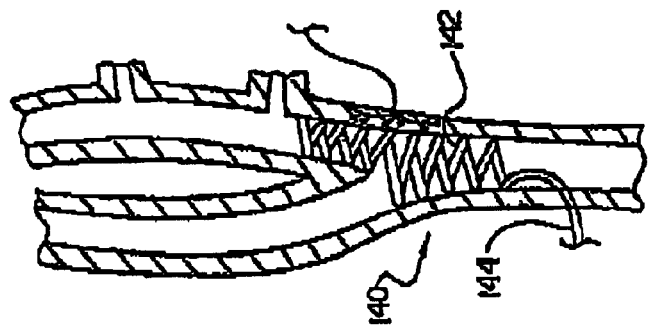
Fig. 6A
Fig. 6B
Fig. 6C
Fig. 6D

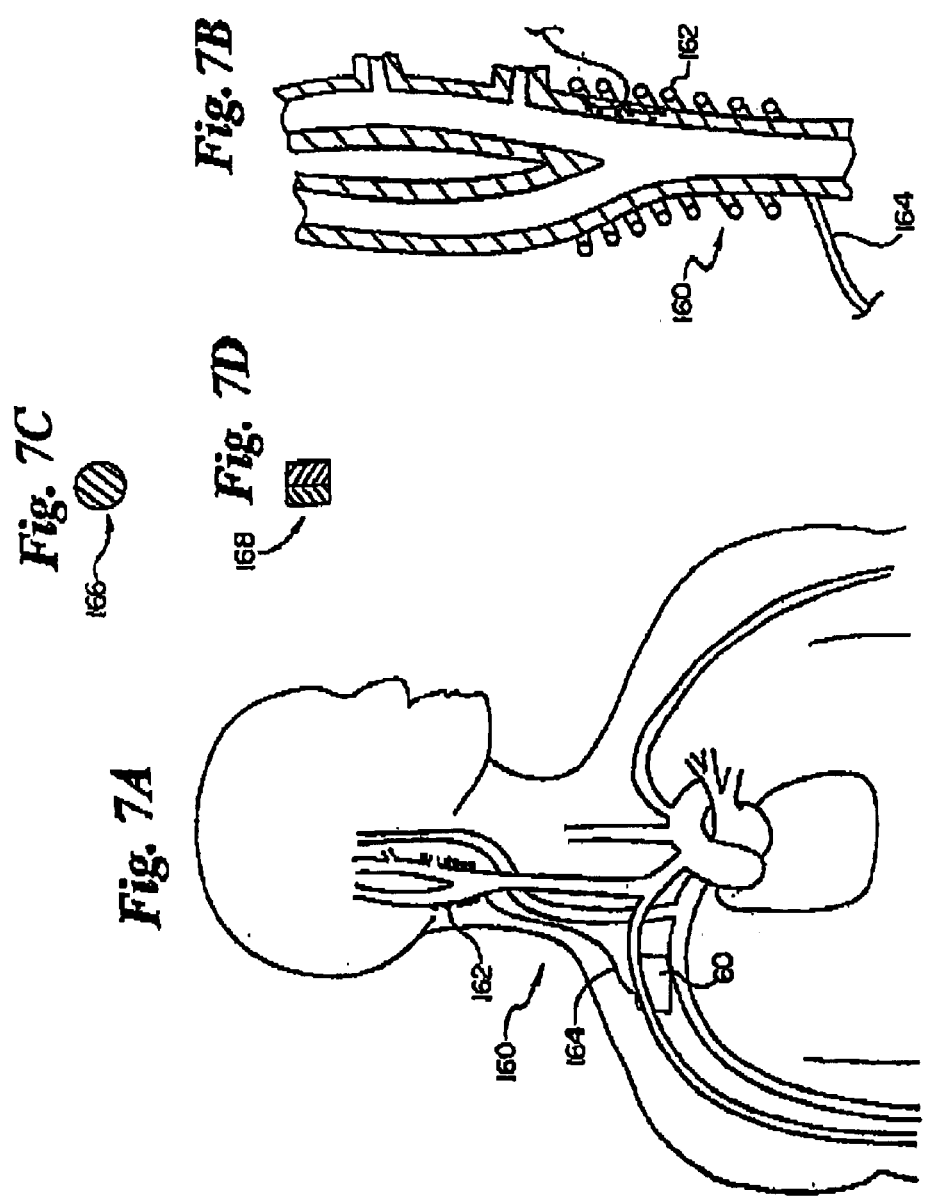

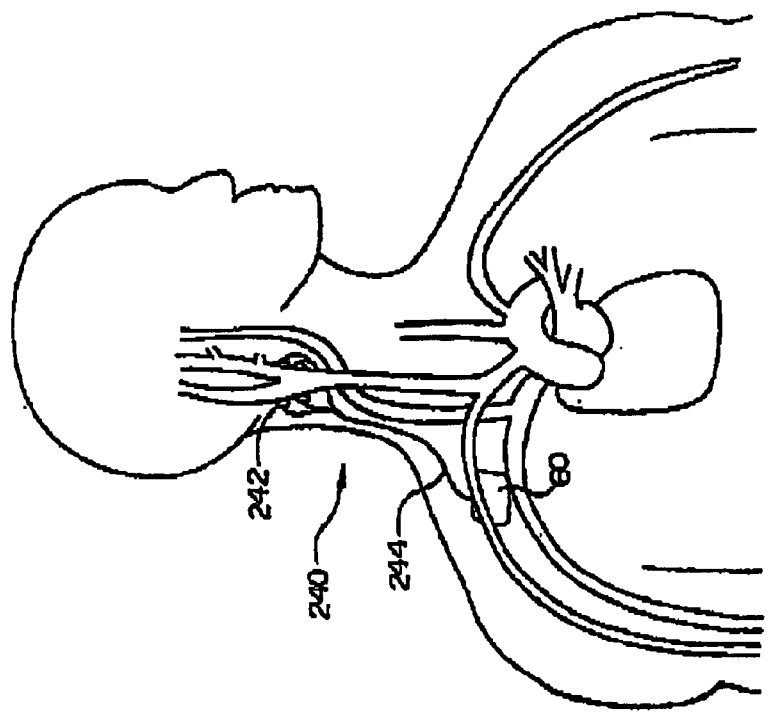
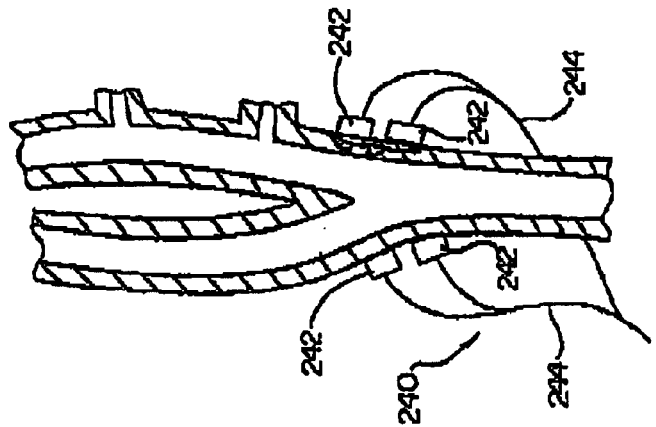
Fig. 11A
Fig. 11B

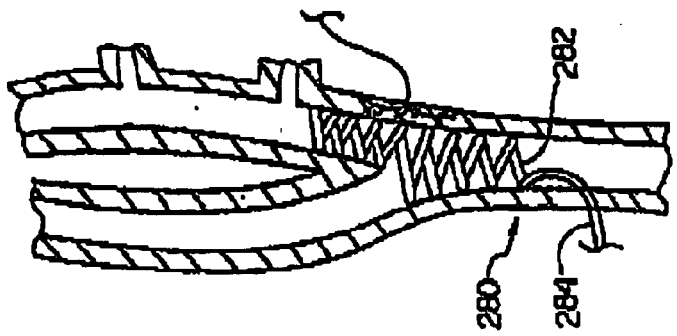
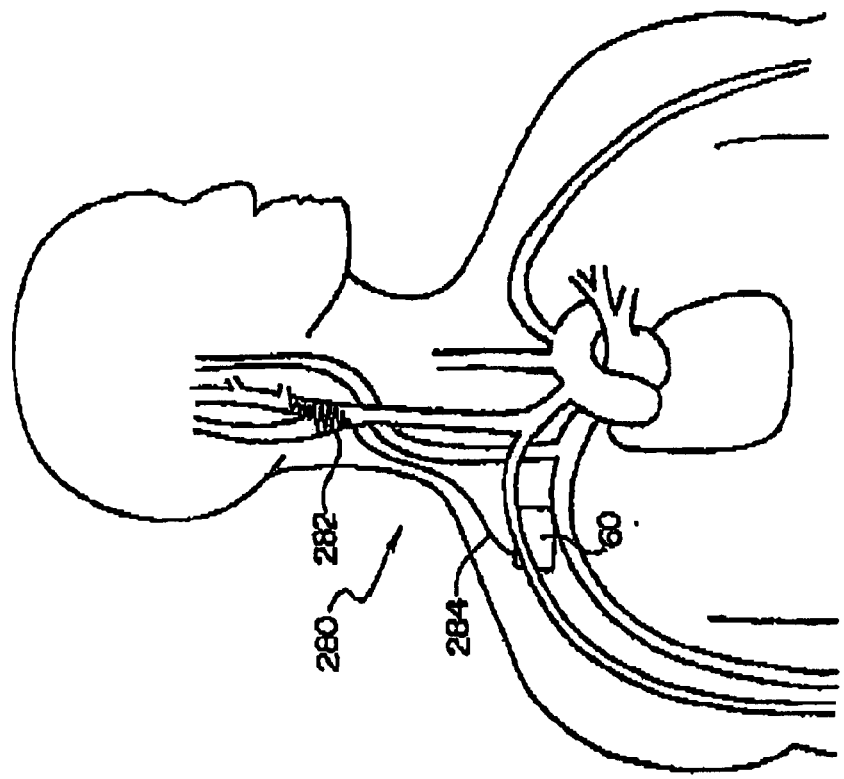

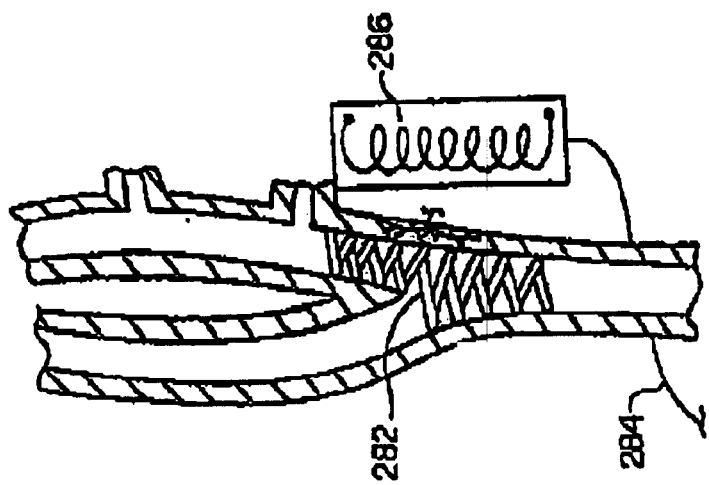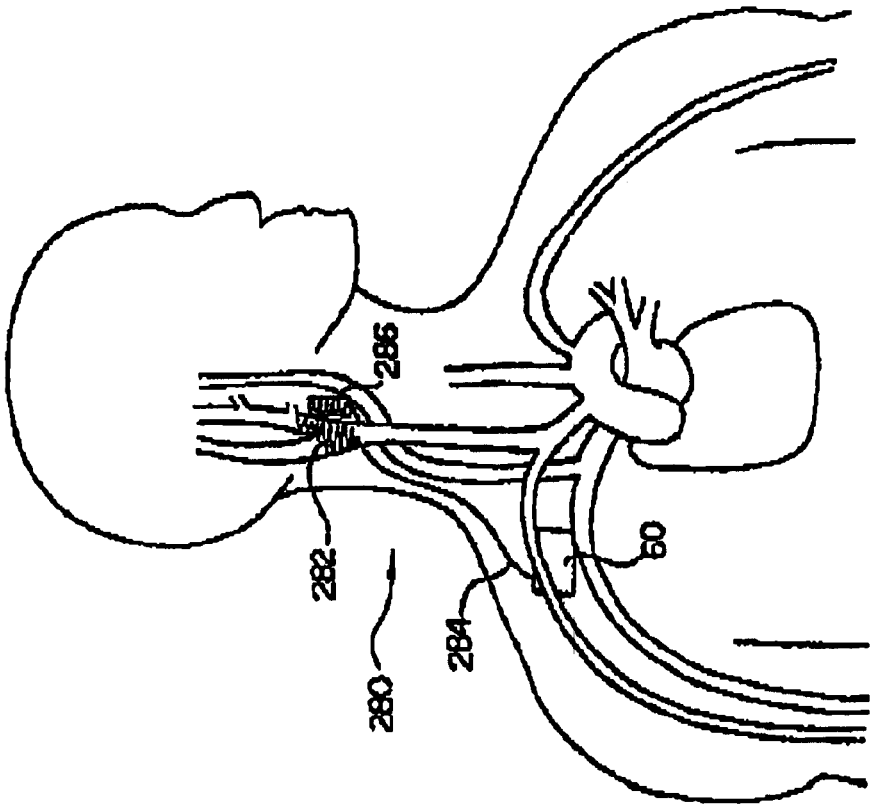

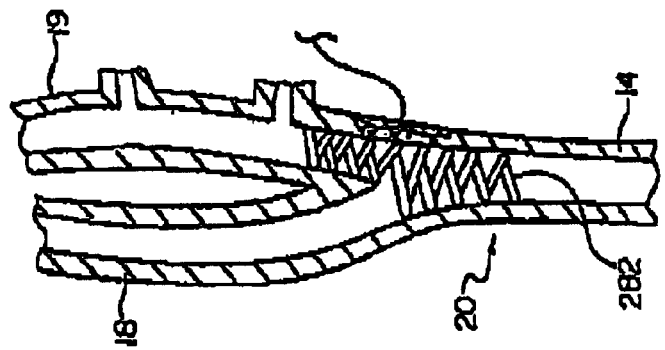
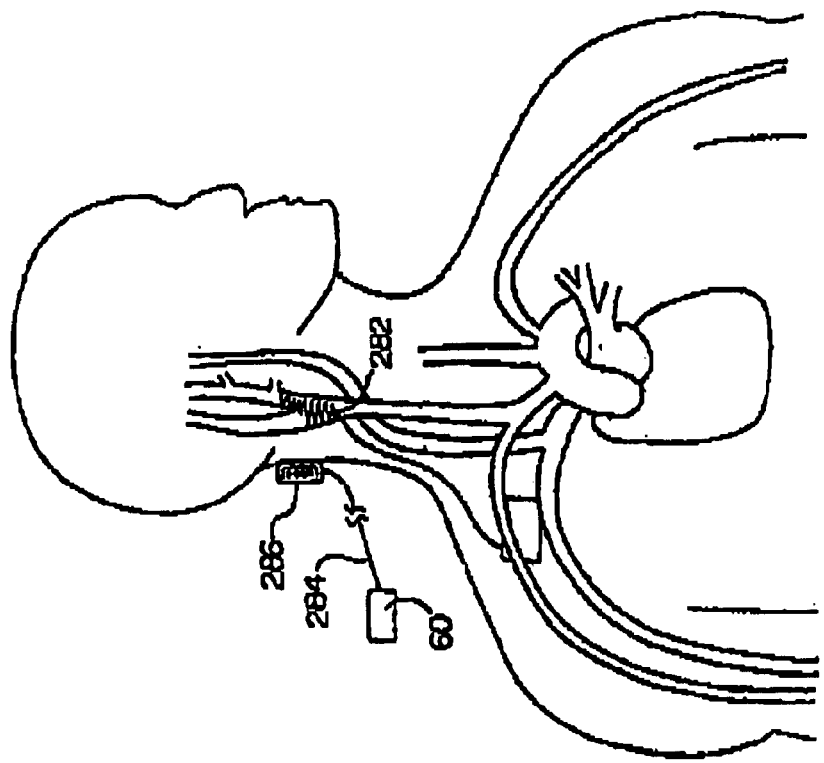

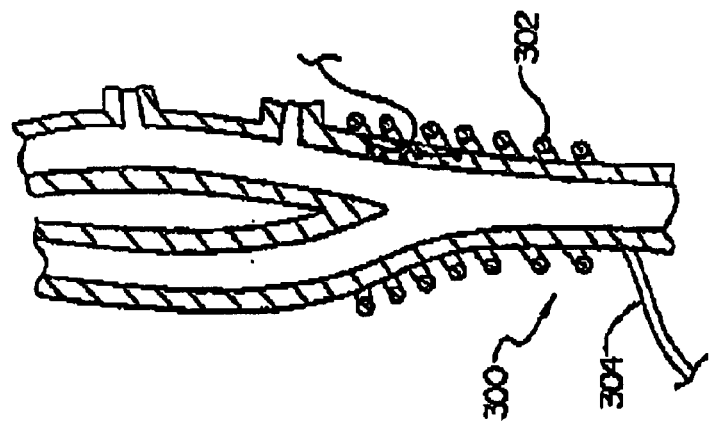
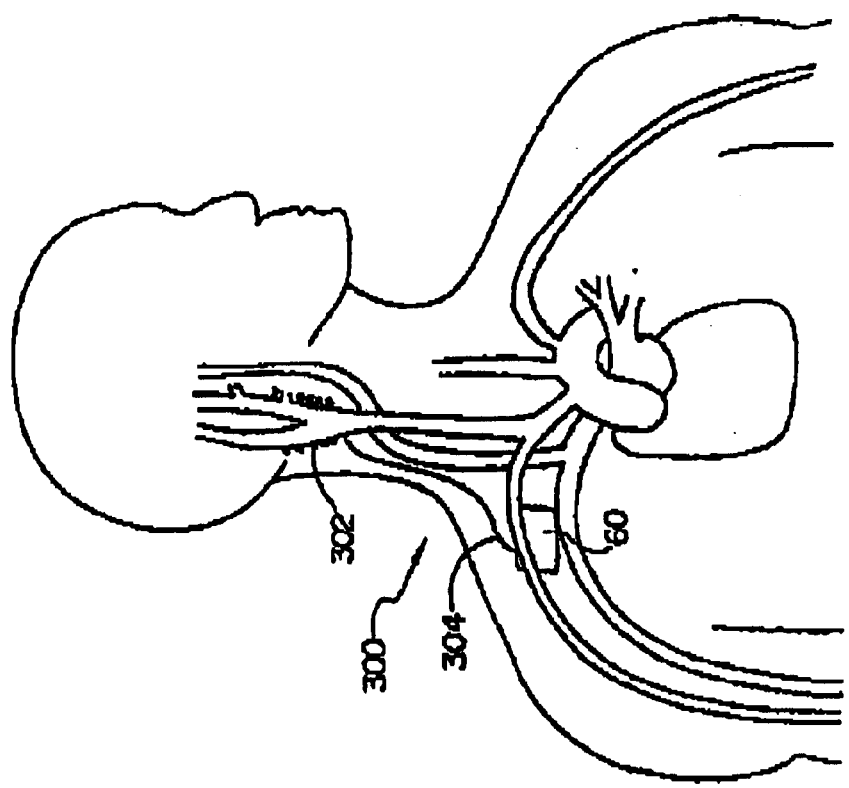

MAPPING METHODS FOR CARDIOVASCULAR REFLEX CONTROL DEVICES

CROSS REFERENCE TO CO-PENDING PATENT APPLICATIONS

This application claims priority to U.S. patent application Ser. No. 09/671,850, filed Sep. 27, 2000, entitled "Devices and Methods for Cardiovascular Reflex Control", U.S. patent application Ser. No. 09/963,777, filed on even date herewith, entitled "Electrode Designs and Methods of Use for Cardiovascular Reflex Control Devices", and U.S. patent application Ser. No. 09/964,079, filed on even date herewith, entitled "Stimulus Regimens for Cardiovascular Reflex Control", the entire disclosures of which are hereby incorporated by reference.

FIELD OF THE INVENTION

The present invention generally relates to medical devices and methods of use for the treatment and/or management of cardiovascular and renal disorders. Specifically, the present invention relates to devices and methods for controlling the baroreflex system for the treatment and/or management of cardiovascular and renal disorders and their underlying causes and conditions.

BACKGROUND OF THE INVENTION

Cardiovascular disease is a major contributor to patient illness and mortality. It also is a primary driver of health care expenditure, costing more than $326 billion each year in the United States. Hypertension, or high blood pressure, is a major cardiovascular disorder that is estimated to affect over 50 million people in the United Sates alone. Of those with hypertension, it is reported that fewer than 30% have their blood pressure under control. Hypertension is a leading cause of heart failure and stroke. It is the primary cause of death in over 42,000 patients per year and is listed as a primary or contributing cause of death in over 200,000 patients per year in the U.S. Accordingly, hypertension is a serious health problem demanding significant research and development for the treatment thereof.

Hypertension may occur when the body's smaller blood vessels (arterioles) constrict, causing an increase in blood pressure. Because the blood vessels constrict, the heart must work harder to maintain blood flow at the higher pressures. Although the body may tolerate short periods of increased blood pressure, sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke. Sustained high blood pressure may eventually result in an enlarged and damaged heart (hypertrophy), which may lead to heart failure.

Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year. It is also estimated that greater than 400,000 new cases of heart failure are diagnosed each year. Heart failure accounts for over 900,000 hospital admissions annually, and is the most common discharge diagnosis in patients over the age of 65 years. It has been reported that the cost of treating heart failure in the United States exceeds $20 billion annually. Accordingly, heart failure is also a serious health problem demanding significant research and development for the treatment and/or management thereof.

Heart failure results in the activation of a number of body systems to compensate for the heart's inability to pump sufficient blood. Many of these responses are mediated by an increase in the level of activation of the sympathetic nervous system, as well as by activation of multiple other neurohormonal responses. Generally speaking, this sympathetic nervous system activation signals the heart to increase heart rate and force of contraction to increase the cardiac output; it signals the kidneys to expand the blood volume by retaining sodium and water; and it signals the arterioles to constrict to elevate the blood pressure. The cardiac, renal and vascular responses increase the workload of the heart, further accelerating myocardial damage and exacerbating the heart failure state. Accordingly, it is desirable to reduce the level of sympathetic nervous system activation in order to stop or at least minimize this vicious cycle and thereby treat or manage the heart failure.

A number of drug treatments have been proposed for the management of hypertension, heart failure and other cardiovascular disorders. These include vasodilators to reduce the blood pressure and ease the workload of the heart, diuretics to reduce fluid overload, inhibitors and blocking agents of the body's neurohormonal responses, and other medicaments.

Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month. Other surgical procedures are available as well.

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through activation of the sympathetic nervous system. Electrical stimulation of the carotid sinus nerve (baropacing) has previously been proposed to reduce blood pressure and the workload of the heart in the treatment of high blood pressure and angina. For example, U.S. Pat. No. 6,073,048 to Kieval et al. discloses a baroreflex modulation system and method for stimulating the baroreflex arc based on various cardiovascular and pulmonary parameters.

Although each of these alternative approaches is beneficial in some ways, each of the therapies has its own disadvantages. For example, drug therapy is often incompletely effective. Some patients may be unresponsive (refractory) to medical therapy. Drugs often have unwanted side effects and may need to be given in complex regimens. These and other factors contribute to poor patient compliance with medical therapy. Drug therapy may also be expensive, adding to the health care costs associated with these disorders. Likewise, surgical approaches are very costly, may be associated with significant patient morbidity and mortality and may not alter the natural history of the disease. Baropacing also has not gained acceptance. Several problems with electrical carotid sinus nerve stimulation have been reported in the medical literature. These include the invasiveness of the surgical procedure to implant the nerve electrodes, and postoperative pain in the jaw, throat, face and head during stimulation. In addition, it has been noted that high voltages sometimes required for nerve stimulation may damage the carotid sinus nerves. Accordingly, there continues to be a substantial and long felt need for new devices and methods for treating and/or managing high blood pressure, heart failure and their associated cardiovascular and nervous system disorders.

Situations may also arise in which it would be beneficial to raise the blood pressure of a patient. For example, the patient may be experiencing a period of reduced blood pressure, or hypotension. Conditions associated with symptomatic hypotension include vasovagal reactions, orthostatic hypotension and dysautonomia. Alternatively, it may be advantageous to augment the blood pressure of a patient in whom the blood pressure may be normal or near normal, for example in claudication syndromes. Therefore, a also need exists for a therapy that can acutely increase the blood pressure in a patient.

SUMMARY OF THE INVENTION

To address hypertension, heart failure and their associated cardiovascular and nervous system disorders, the present invention provides a number of devices, systems and methods by which the blood pressure, nervous system activity, and neurohormonal activity may be selectively and controllably regulated by activating baroreceptors. By selectively and controllably activating baroreceptors, the present invention reduces excessive blood pressure, sympathetic nervous system activation and neurohormonal activation, thereby minimizing their deleterious effects on the heart, vasculature and other organs and tissues.

In an exemplary embodiment, the present invention provides a system and method for treating a patient by inducing a baroreceptor signal to affect a change in the baroreflex system (e.g., reduced heart rate, reduced blood pressure, etc.). The baroreceptor signal is activated or otherwise modified by selectively activating baroreceptors. To accomplish this, the system and method of the present invention utilize a baroreceptor activation device positioned near a baroreceptor in the carotid sinus, aortic arch, heart, common carotid arteries, subclavian arteries, and/or brachiocephalic artery. Preferably, the baroreceptor activation device is located in the right and/or left carotid sinus (near the bifurcation of the common carotid artery) and/or the aortic arch. By way of example, not limitation, the present invention is described with reference to the carotid sinus location.

Generally speaking, the baroreceptor activation device may be activated, deactivated or otherwise modulated to activate one or more baroreceptors and induce a baroreceptor signal or a change in the baroreceptor signal to thereby affect a change in the baroreflex system. The baroreceptor activation device may be activated, deactivated, or otherwise modulated continuously, periodically, or episodically. The baroreceptor activation device may comprise a wide variety of devices which utilize mechanical, electrical, thermal, chemical, biological, or other means to activate the baroreceptor. The baroreceptor may be activated directly, or activated indirectly via the adjacent vascular tissue. The baroreceptor activation device may be positioned inside the vascular lumen (i.e., intravascularly), outside the vascular wall (i.e., extravascularly) or within the vascular wall (i.e., intramurally). To maximize therapeutic efficacy, a mapping method may be employed to precisely locate or position the baroreceptor activation device.

A control system may be used to generate a control signal which activates, deactivates or otherwise modulates the baroreceptor activation device. The control system may operate in an open-loop or a closed-loop mode. For example, in the open-loop mode, the patient and/or physician may directly or remotely interface with the control system to prescribe the control signal. In the closed-loop mode, the control signal may be responsive to feedback from a sensor, wherein the response is dictated by a preset or programmable algorithm.

To address low blood pressure and other conditions requiring blood pressure augmentation, the present invention provides a number of devices, systems and methods by which the blood pressure may be selectively and controllably regulated by inhibiting or dampening baroreceptor signals. By selectively and controllably inhibiting or dampening baroreceptor signals, the present invention reduces conditions associated with low blood pressure.

BRIEF DESCRIPTION OF THE DRAWINGS

FIG. 2A is a cross-sectional schematic illustration of the carotid sinus and baroreceptors within the vascular wall;

FIG. 2B is a schematic illustration of baroreceptors within the vascular wall and the baroreflex system;

FIGS. 6A and 6B are schematic illustrations of a baroreceptor activation device in the form of an internal deformable coil structure which mechanically induces a baroreceptor signal in accordance with an embodiment of the present invention;

FIGS. 6C and 6D are cross-sectional views of alternative embodiments of the coil member illustrated in FIGS. 6A and 6B;

FIGS. 7A and 7B are schematic illustrations of a baroreceptor activation device in the form of an external deformable coil structure which mechanically induces a baroreceptor signal in accordance with an embodiment of the present invention;

FIGS. 7C and 7D are cross-sectional views of alternative embodiments of the coil member illustrated in FIGS. 7A and 7B;

FIGS. 11A and 11B are schematic illustrations of a baroreceptor activation device in the form of a transducer which mechanically induces a baroreceptor signal in accordance with an embodiment of the present invention;

FIGS. 13A and 13B are schematic illustrations of a baroreceptor activation device in the form of an internal conductive structure which electrically or thermally induces a baroreceptor signal in accordance with an embodiment of the present invention;

FIGS. 14A and 14B are schematic illustrations of a baroreceptor activation device in the form of an internal conductive structure, activated by an internal inductor, which electrically or thermally induces a baroreceptor signal in accordance with an embodiment of the present invention;

FIGS. 16A and 16B are schematic illustrations of a baroreceptor activation device in the form of an internal conductive structure, activated by an external inductor, which electrically or thermally induces a baroreceptor signal in accordance with an embodiment of the present invention;

FIGS. 17A and 17B are schematic illustrations of a baroreceptor activation device in the form of an external conductive structure which electrically or thermally induces a baroreceptor signal in accordance with an embodiment of the present invention;

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
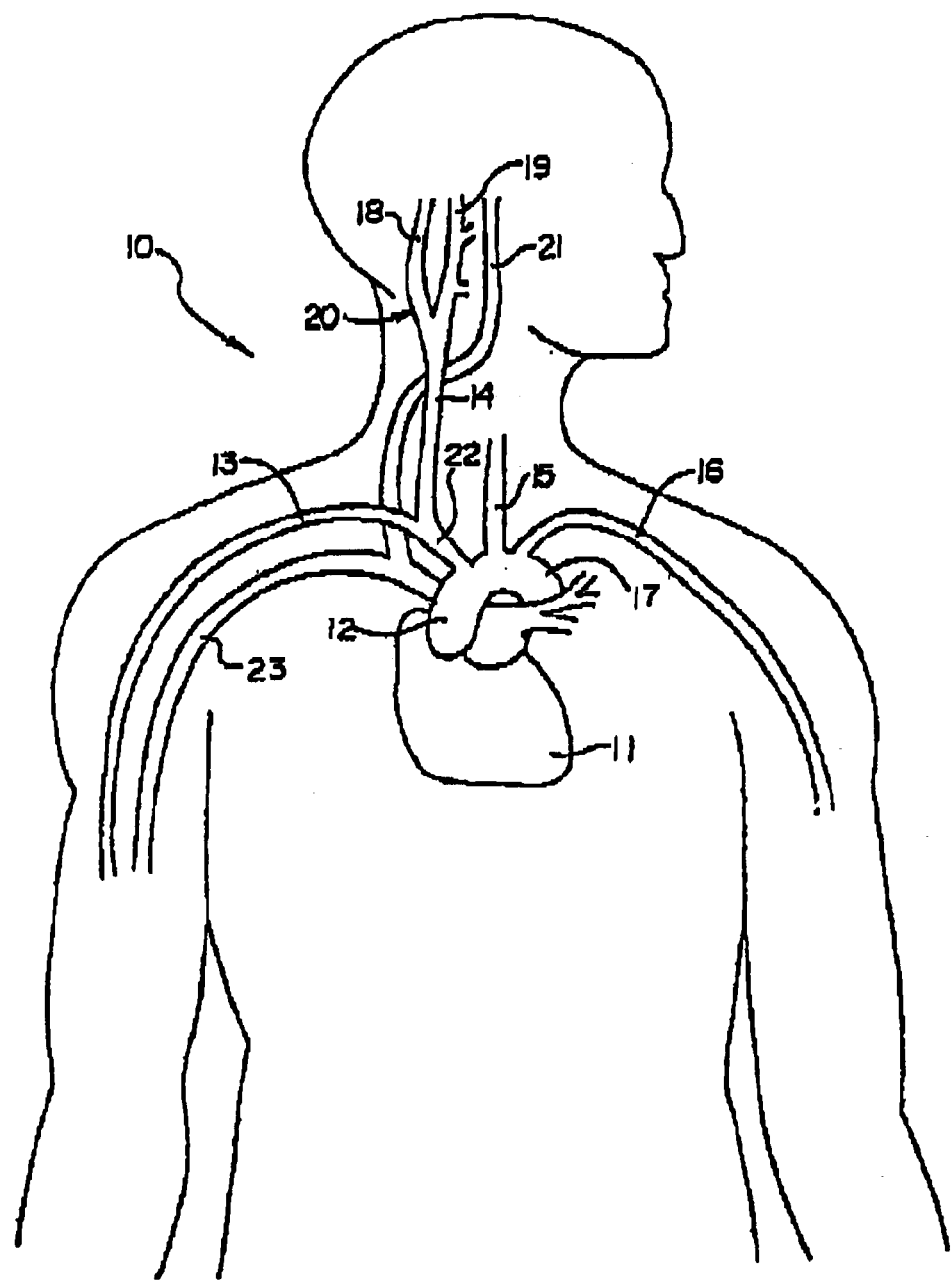
FIG. 1 is a schematic illustration of the upper torso of a human body showing the major arteries and veins and associated anatomy.

To better understand the present invention, it may be useful to explain some of the basic vascular anatomy associated with the cardiovascular system. Refer to FIG. 1 which is a schematic illustration of the upper torso of a human body 10 showing some of the major arteries and veins of the cardiovascular system. The left ventricle of the heart 11 pumps oxygenated blood up into the aortic arch 12. The right subclavian artery 13, the right common carotid artery 14, the left common carotid artery 15 and the left subclavian artery 16 branch off the aortic arch 12 proximal of the descending thoracic aorta 17. Although relatively short, a distinct vascular segment referred to as the brachiocephalic artery 22 connects the right subclavian artery 13 and the right common carotid artery 14 to the aortic arch 12. The right carotid artery 14 bifurcates into the right external carotid artery 18 and the right internal carotid artery 19 at the right carotid sinus 20. Although not shown for purposes of clarity only, the left carotid artery 15 similarly bifurcates into the left external carotid artery and the left internal carotid artery at the left carotid sinus.

From the aortic arch 12, oxygenated blood flows into the carotid arteries 18/19 and the subclavian arteries 13/16. From the carotid arteries 18/19, oxygenated blood circulates through the head and cerebral vasculature and oxygen depleted blood returns to the heart 11 by way of the jugular veins, of which only the right internal jugular vein 21 is shown for sake of clarity. From the subclavian arteries 13/16, oxygenated blood circulates through the upper peripheral vasculature and oxygen depleted blood returns to the heart by way of the subclavian veins, of which only the right subclavian vein 23 is shown, also for sake of clarity. The heart 11 pumps the oxygen depleted blood through the pulmonary system where it is re-oxygenated. The re-oxygenated blood returns to the heart 11 which pumps the re-oxygenated blood into the aortic arch as described above, and the cycle repeats.

Within the arterial walls of the aortic arch 12, common carotid arteries 14/15 (near the right carotid sinus 20 and left carotid sinus), subclavian arteries 13/16 and brachiocephalic artery 22 there are baroreceptors 30. For example, as best seen in FIG. 2A, baroreceptors 30 reside within the vascular walls of the carotid sinus 20. Baroreceptors 30 are a type of stretch receptor used by the body to sense blood pressure. An increase in blood pressure causes the arterial wall to stretch, and a decrease in blood pressure causes the arterial wall to return to its original size. Such a cycle is repeated with each beat of the heart. Because baroreceptors 30 are located within the arterial wall, they are able to sense deformation of the adjacent tissue, which is indicative of a change in blood pressure. The baroreceptors 30 located in the right carotid sinus 20, the left carotid sinus and the aortic arch 12 play the most significant role in sensing blood pressure that affects the baroreflex system 50, which is described in more detail with reference to FIG. 2B.

Refer now to FIG. 2B, which shows a schematic illustration of baroreceptors 30 disposed in a generic vascular wall 40 and a schematic flow chart of the baroreflex system 50. Baroreceptors 30 are profusely distributed within the arterial walls 40 of the major arteries discussed previously, and generally form an arbor 32. The baroreceptor arbor 32 comprises a plurality of baroreceptors 30, each of which transmits baroreceptor signals to the brain 52 via nerve 38. The baroreceptors 30 are so profusely distributed and arborized within the vascular wall 40 that discrete baroreceptor arbors 32 are not readily discernable. To this end, those skilled in the art will appreciate that the baroreceptors 30 shown in FIG. 2B are primarily schematic for purposes of illustration and discussion.

Baroreceptor signals are used to activate a number of body systems which collectively may be referred to as the baroreflex system 50. Baroreceptors 30 are connected to the brain 52 via the nervous system 51. Thus, the brain 52 is able to detect changes in blood pressure, which is indicative of cardiac output. If cardiac output is insufficient to meet demand (i.e., the heart 11 is unable to pump sufficient blood), the baroreflex system 50 activates a number of body systems, including the heart 11, kidneys 53, vessels 54, and other organs/tissues. Such activation of the baroreflex system 50 generally corresponds to an increase in neurohormonal activity. Specifically, the baroreflex system 50 initiates a neurohormonal sequence that signals the heart 11 to increase heart rate and increase contraction force in order to increase cardiac output, signals the kidneys 53 to increase blood volume by retaining sodium and water, and signals the vessels 54 to constrict to elevate blood pressure. The cardiac, renal and vascular responses increase blood pressure and cardiac output 55, and thus increase the workload of the heart 11. In a patient with heart failure, this further accelerates myocardial damage and exacerbates the heart failure state.

To address the problems of hypertension, heart failure, other cardiovascular disorders and renal disorders, the present invention basically provides a number of devices, systems and methods by which the baroreflex system 50 is activated to reduce excessive blood pressure, autonomic nervous system activity and neurohormonal activation. In particular, the present invention provides a number of devices, systems and methods by which baroreceptors 30 may be activated, thereby indicating an increase in blood pressure and signaling the brain 52 to reduce the body's blood pressure and level of sympathetic nervous system and neurohormonal activation, and increase parasypathetic nervous system activation, thus having a beneficial effect on the cardiovascular system and other body systems.

Figure 3:
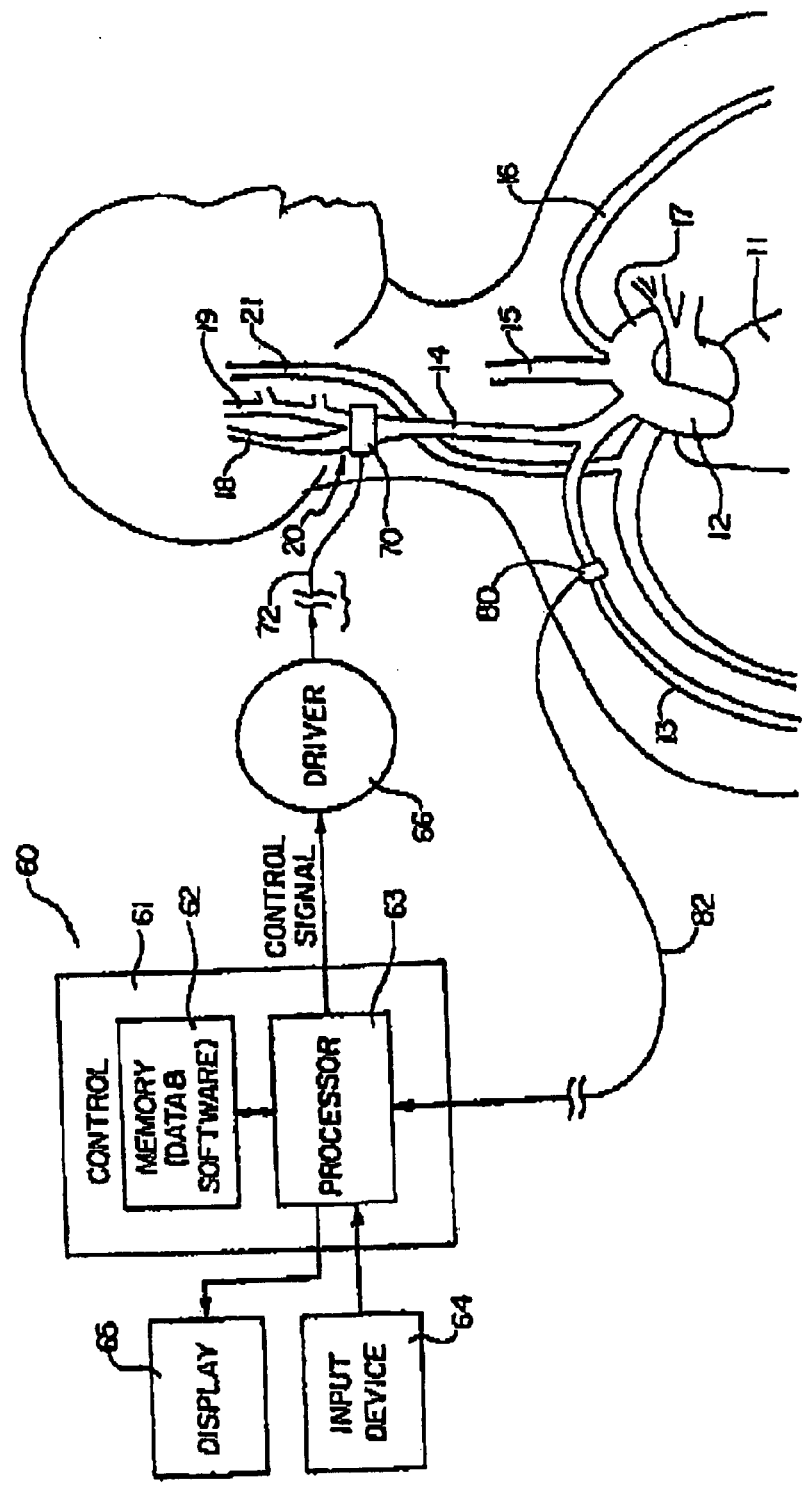
FIG. 3 is a schematic illustration of a baroreceptor activation system in accordance with the present invention.

With reference to FIG. 3, the present invention generally provides a system including a control system 60, a baroreceptor activation device 70, and a sensor 80 (optional), which generally operate in the following manner. The sensor 80 senses and/or monitors a parameter (e.g., cardiovascular function) indicative of the need to modify the baroreflex system and generates a signal indicative of the parameter. The control system 60 generates a control signal as a function of the received sensor signal. The control signal activates, deactivates or otherwise modulates the baroreceptor activation device 70. Typically, activation of the device 70 results in activation of the baroreceptors 30. Alternatively, deactivation or modulation of the baroreceptor activation device 70 may cause or modify activation of the baroreceptors 30. The baroreceptor activation device 70 may comprise a wide variety of devices which utilize mechanical, electrical, thermal, chemical, biological, or other means to activate baroreceptors 30. Thus, when the sensor 80 detects a parameter indicative of the need to modify the baroreflex system activity (e.g., excessive blood pressure), the control system 60 generates a control signal to modulate (e.g. activate) the baroreceptor activation device 70 thereby inducing a baroreceptor 30 signal that is perceived by the brain 52 to be apparent excessive blood pressure. When the sensor 80 detects a parameter indicative of normal body function (e.g., normal blood pressure), the control system 60 generates a control signal to modulate (e.g., deactivate) the baroreceptor activation device 70.

As mentioned previously, the baroreceptor activation device 70 may comprise a wide variety of devices which utilize mechanical, electrical, thermal, chemical, biological or other means to activate the baroreceptors 30. Specific embodiments of the generic baroreceptor activation device 70 are discussed with reference to FIGS. 4–21. In most instances, particularly the mechanical activation embodiments, the baroreceptor activation device 70 indirectly activates one or more baroreceptors 30 by stretching or otherwise deforming the vascular wall 40 surrounding the baroreceptors 30. In some other instances, particularly the non-mechanical activation embodiments, the baroreceptor activation device 70 may directly activate one or more baroreceptors 30 by changing the electrical, thermal or chemical environment or potential across the baroreceptors 30. It is also possible that changing the electrical, thermal or chemical potential across the tissue surrounding the baroreceptors 30 may cause the surrounding tissue to stretch or otherwise deform, thus mechanically activating the baroreceptors 30. In other instances, particularly the biological activation embodiments, a change in the function or sensitivity of the baroreceptors 30 may be induced by changing the biological activity in the baroreceptors 30 and altering their intracellular makeup and function.

All of the specific embodiments of the baroreceptor activation device 70 are suitable for implantation, and are preferably implanted using a minimally invasive percutaneous translumenal approach and/or a minimally invasive surgical approach, depending on whether the device 70 is disposed intravascularly, extravascularly or within the vascular wall 40. The baroreceptor activation device 70 may be positioned anywhere baroreceptors 30 affecting the baroreflex system 50 are numerous, such as in the heart 11, in the aortic arch 12, in the common carotid arteries 18/19 near the carotid sinus 20, in the subclavian arteries 13/16, or in the brachiocephalic artery 22. The baroreceptor activation device 70 may be implanted such that the device 70 is positioned immediately adjacent the baroreceptors 30. Alternatively, the baroreceptor activation device 70 may be outside the body such that the device 70 is positioned a short distance from but proximate to the baroreceptors 30. Preferably, the baroreceptor activation device 70 is implanted near the right carotid sinus 20 and/or the left carotid sinus (near the bifurcation of the common carotid artery) and/or the aortic arch 12, where baroreceptors 30 have a significant impact on the baroreflex system 50. For purposes of illustration only, the present invention is described with reference to baroreceptor activation device 70 positioned near the carotid sinus 20.

The optional sensor 80 is operably coupled to the control system 60 by electric sensor cable or lead 82. The sensor 80 may comprise any suitable device that measures or monitors a parameter indicative of the need to modify the activity of the baroreflex system. For example, the sensor 80 may comprise a physiologic transducer or gauge that measures ECG, blood pressure (systolic, diastolic, average or pulse pressure), blood volumetric flow rate, blood flow velocity, blood pH, $O_2$ or $CO_2$ content, mixed venous oxygen saturation ($SVO_2$), vasoactivity, nerve activity, tissue activity or composition. Examples of suitable transducers or gauges for the sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, a membrane pH electrode, an optical detector ($SVO_2$) or a strain gage. Although only one sensor 80 is shown, multiple sensors 80 of the same or different type at the same or different locations may be utilized.

The sensor 80 is preferably positioned in a chamber of the heart 11, or in/on a major artery such as the aortic arch 12, a common carotid artery 14/15, a subclavian artery 13/16 or the brachiocephalic artery 22, such that the parameter of interest may be readily ascertained. The sensor 80 may be disposed inside the body such as in or on an artery, a vein or a nerve (e.g. vagus nerve), or disposed outside the body, depending on the type of transducer or gauge utilized. The sensor 80 may be separate from the baroreceptor activation device 70 or combined therewith. For purposes of illustration only, the sensor 80 is shown positioned on the right subclavian artery 13.

By way of example, the control system 60 includes a control block 61 comprising a processor 63 and a memory 62. Control system 60 is connected to the sensor 80 by way of sensor cable 82. Control system 60 is also connected to the baroreceptor activation device 70 by way of electric control cable 72. Thus, the control system 60 receives a sensor signal from the sensor 80 by way of sensor cable 82, and transmits a control signal to the baroreceptor activation device 70 by way of control cable 72.

The memory 62 may contain data related to the sensor signal, the control signal, and/or values and commands provided by the input device 64. The memory 62 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value or when the sensor signal indicates a specific physiologic event.

As mentioned previously, the baroreceptor activation device 70 may activate baroreceptors 30 mechanically, electrically, thermally, chemically, biologically or otherwise. In some instances, the control system 60 includes a driver 66 to provide the desired power mode for the baroreceptor activation device 70. For example if the baroreceptor activation device 70 utilizes pneumatic or hydraulic actuation, the driver 66 may comprise a pressure/vacuum source and the cable 72 may comprise fluid line(s). If the baroreceptor activation device 70 utilizes electrical or thermal actuation, the driver 66 may comprise a power amplifier or the like and the cable 72 may comprise electrical lead(s). If the baroreceptor activation device 70 utilizes chemical or biological actuation, the driver 66 may comprise a fluid reservoir and a pressure/vacuum source, and the cable 72 may comprise fluid line(s). In other instances, the driver 66 may not be necessary, particularly if the processor 63 generates a sufficiently strong electrical signal for low level electrical or thermal actuation of the baroreceptor activation device 70.

The control system 60 may operate as a closed loop utilizing feedback from the sensor 80, or as an open loop utilizing commands received by input device 64. The open loop operation of the control system 60 preferably utilizes some feedback from the transducer 80, but may also operate without feedback. Commands received by the input device 64 may directly influence the control signal or may alter the software and related algorithms contained in memory 62. The patient and/or treating physician may provide commands to input device 64. Display 65 may be used to view the sensor signal, control signal and/or the software/data contained in memory 62.

The control signal generated by the control system 60 may be continuous, periodic, episodic or a combination thereof, as dictated by an algorithm contained in memory 62. Continuous control signals include a constant pulse, a constant train of pulses, a triggered pulse and a triggered train of pulses. Examples of periodic control signals include each of the continuous control signals described above which have a designated start time (e.g., beginning of each minute, hour or day) and a designated duration (e.g., 1 second, 1 minute, 1 hour). Examples of episodic control signals include each of the continuous control signals described above which are triggered by an episode (e.g., activation by the patient/physician, an increase in blood pressure above a certain threshold, etc.).

The control system 60 may be implanted in whole or in part. For example, the entire control system 60 may be carried externally by the patient utilizing transdermal connections to the sensor lead 82 and the control lead 72. Alternatively, the control block 61 and driver 66 may be implanted with the input device 64 and display 65 carried externally by the patient utilizing transdermal connections therebetween. As a further alternative, the transdermal connections may be replaced by cooperating transmitters/receivers to remotely communicate between components of the control system 60 and/or the sensor 80 and baroreceptor activation device 70.

With general reference to FIGS. 4–21, schematic illustrations of specific embodiments of the baroreceptor activation device 70 are shown. The design, function and use of these specific embodiments, in addition to the control system 60 and sensor 80 (not shown), are the same as described with reference to FIG. 3, unless otherwise noted or apparent from the description. In addition, the anatomical features illustrated in FIGS. 4–20 are the same as discussed with reference to FIGS. 1, 2A and 2B, unless otherwise noted. In each embodiment, the connections between the components 60/70/80 may be physical (e.g., wires, tubes, cables, etc.) or remote (e.g., transmitter/receiver, inductive, magnetic, etc.). For physical connections, the connection may travel intraarterially, intravenously, subcutaneously, or through other natural tissue paths.

Figure 4B:
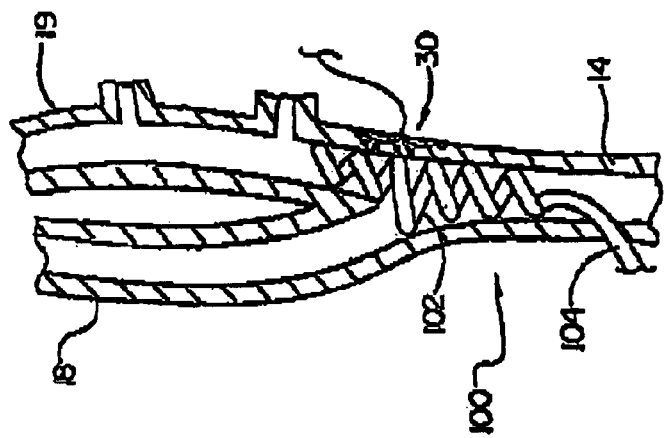
FIGS. 4A and 4B are schematic illustrations of a baroreceptor activation device in the form of an internal inflatable balloon which mechanically induces a baroreceptor signal in accordance with an embodiment of the present invention.
Figure 4A:
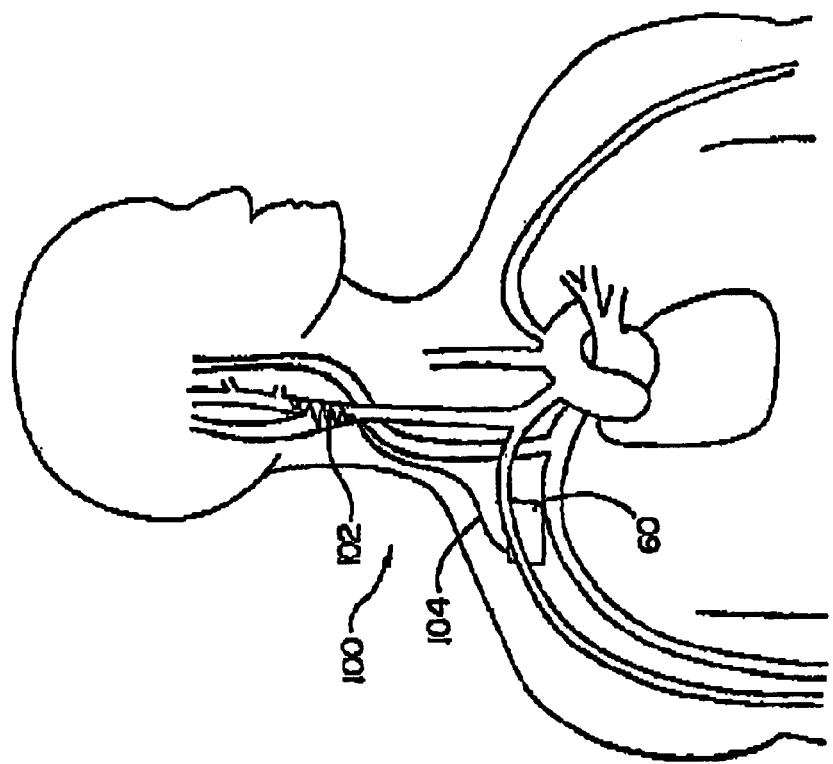

Refer now to FIGS. 4A and 4B which show schematic illustrations of a baroreceptor activation device 100 in the form of an intravascular inflatable balloon. The inflatable balloon device 100 includes a helical balloon 102 which is connected to a fluid line 104. An example of a similar helical balloon is disclosed in U.S. Pat. No. 5,181,911 to Shturman, the entire disclosure of which is hereby incorporated by reference. The balloon 102 preferably has a helical geometry or any other geometry which allows blood perfusion therethrough. The fluid line 104 is connected to the driver 66 of the control system 60. In this embodiment, the driver 66 comprises a pressure/vacuum source (i.e., an inflation device) which selectively inflates and deflates the helical balloon 102. Upon inflation, the helical balloon 102 expands, preferably increasing in outside diameter only, to mechanically activate baroreceptors 30 by stretching or otherwise deforming them and/or the vascular wall 40. Upon deflation, the helical balloon 102 returns to its relaxed geometry such that the vascular wall 40 returns to its nominal state. Thus, by selectively inflating the helical balloon 102, the baroreceptors 30 adjacent thereto may be selectively activated.

As an alternative to pneumatic or hydraulic expansion utilizing a balloon, a mechanical expansion device (not shown) may be used to expand or dilate the vascular wall 40 and thereby mechanically activate the baroreceptors 30. For example, the mechanical expansion device may comprise a tubular wire braid structure that diametrically expands when longitudinally compressed as disclosed in U.S. Pat. No. 5,222,971 to Willard et al., the entire disclosure of which is hereby incorporated by reference. The tubular braid may be disposed intravascularly and permits blood perfusion through the wire mesh. In this embodiment, the driver 66 may comprise a linear actuator connected by actuation cables to opposite ends of the braid. When the opposite ends of the tubular braid are brought closer together by actuation of the cables, the diameter of the braid increases to expand the vascular wall 40 and activate the baroreceptors 30.

Figure 5B:
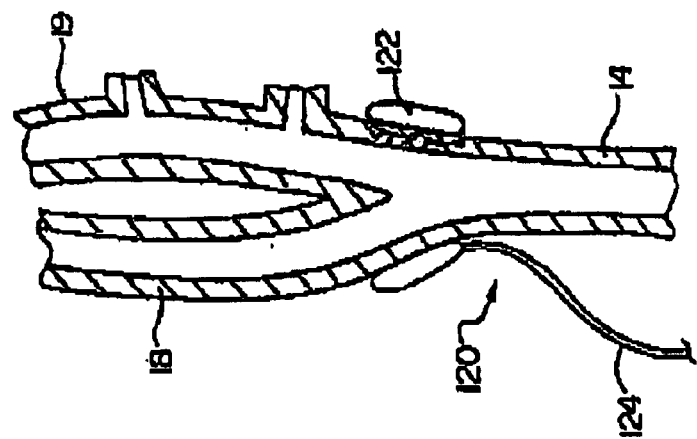
FIGS. 5A and 5B are schematic illustrations of a baroreceptor activation device in the form of an external pressure cuff which mechanically induces a baroreceptor signal in accordance with an embodiment of the present invention.
Figure 5A:
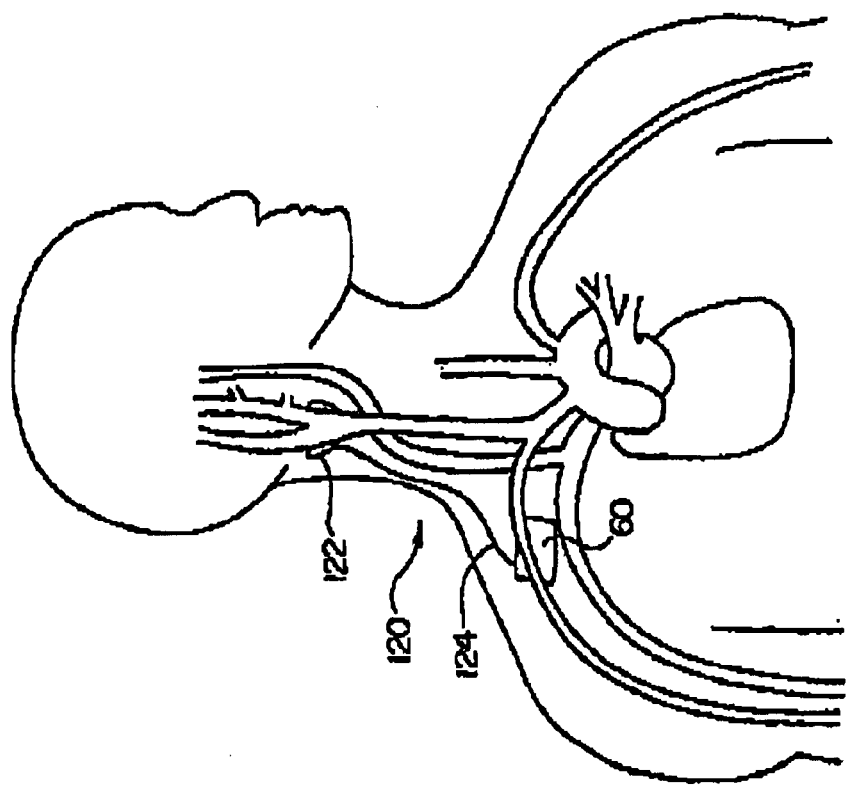

Refer now to FIGS. 5A and 5B which show schematic illustrations of a baroreceptor activation device 120 in the form of an extravascular pressure cuff. The pressure cuff device 120 includes an inflatable cuff 122 which is connected to a fluid line 124. Examples of a similar cuffs 122 are disclosed in U.S. Pat. No. 4,256,094 to Kapp et al. and U.S. Pat. No. 4,881,939 to Newman, the entire disclosures of which are hereby incorporated by reference. The fluid line 124 is connected to the driver 66 of the control system 60. In this embodiment, the driver 66 comprises a pressure/vacuum source (i.e., an inflation device) which selectively inflates and deflates the cuff 122. Upon inflation, the cuff 122 expands, preferably increasing in inside diameter only, to mechanically activate baroreceptors 30 by stretching or otherwise deforming them and/or the vascular wall 40. Upon deflation, the cuff 122 returns to its relaxed geometry such that the vascular wall 40 returns to its nominal state. Thus, by selectively inflating the inflatable cuff 122, the baroreceptors 30 adjacent thereto may be selectively activated.

The driver 66 may be automatically actuated by the control system 60 as discussed above, or may be manually actuated. An example of an externally manually actuated pressure/vacuum source is disclosed in U.S. Pat. No. 4,709,690 to Haber, the entire disclosure of which is hereby incorporated by reference. Examples of transdermally manually actuated pressure/vacuum sources are disclosed in U.S. Pat. No. 4,586,501 to Claracq, U.S. Pat. No. 4,828,544 to Lane et al., and U.S. Pat. No. 5,634,878 to Grundei et al., the entire disclosures of which are hereby incorporated by reference.

Those skilled in the art will recognize that other external compression devices may be used in place of the inflatable cuff device 120. For example, a piston actuated by a solenoid may apply compression to the vascular wall. An example of a solenoid actuated piston device is disclosed in U.S. Pat. No. 4,014,318 to Dokum et al, and an example of a hydraulically or pneumatically actuated piston device is disclosed in U.S. Pat. No. 4,586,501 to Claracq, the entire disclosures of which are hereby incorporated by reference. Other examples include a rotary ring compression device as disclosed in U.S. Pat. No. 4,551,862 to Haber, and an electromagnetically actuated compression ring device as disclosed in U.S. Pat. No. 5,509,888 to Miller, the entire disclosures of which are hereby incorporated by reference.

Refer now to FIGS. 6A and 6B which show schematic illustrations of a baroreceptor activation device 140 in the form of an intravascular deformable structure. The deformable structure device 140 includes a coil, braid or other stent-like structure 142 disposed in the vascular lumen. The deformable structure 142 includes one or more individual structural members connected to an electrical lead 144. Each of the structural members forming deformable structure 142 may comprise a shape memory material 146 (e.g., nickel titanium alloy) as illustrated in FIG. 6C, or a bimetallic material 148 as illustrated in FIG. 6D. The electrical lead 144 is connected to the driver 66 of the control system 60. In this embodiment, the driver 66 comprises an electric power generator or amplifier which selectively delivers electric current to the structure 142 which resistively heats the structural members 146/148. The structure 142 may be unipolar as shown using the surrounding tissue as ground, or bipolar or multipolar using leads connected to either end of the structure 142. Electrical power may also be delivered to the structure 142 inductively as described hereinafter with reference to FIGS. 14–16.

Upon application of electrical current to the shape memory material 146, it is resistively heated causing a phase change and a corresponding change in shape. Upon application of electrical current to the bimetallic material 148, it is resistively heated causing a differential in thermal expansion and a corresponding change in shape. In either case, the material 146/148 is designed such that the change in shape causes expansion of the structure 142 to mechanically activate baroreceptors 30 by stretching or otherwise deforming them and/or the vascular wall 40. Upon removal of the electrical current, the material 146/148 cools and the structure 142 returns to its relaxed geometry such that the baroreceptors 30 and/or the vascular wall 40 return to their nominal state. Thus, by selectively expanding the structure 142, the baroreceptors 30 adjacent thereto may be selectively activated.

Refer now to FIGS. 7A and 7B which show schematic illustrations of a baroreceptor activation device 160 in the form of an extravascular deformable structure. The extravascular deformable structure device 160 is substantially the same as the intravascular deformable structure device 140 described with reference to FIGS. 6A and 6B, except that the extravascular device 160 is disposed about the vascular wall, and therefore compresses, rather than expands, the vascular wall 40. The deformable structure device 160 includes a coil, braid or other stent-like structure 162 comprising one or more individual structural members connected to an electrical lead 164. Each of the structural members may comprise a shape memory material 166 (e.g., nickel titanium alloy) as illustrated in FIG. 7C, or a bimetallic material 168 as illustrated in FIG. 7D. The structure 162 may be unipolar as shown using the surrounding tissue as ground, or bipolar or multipolar using leads connected to either end of the structure 162. Electrical power may also be delivered to the structure 162 inductively as described hereinafter with reference to FIGS. 14–16.

Upon application of electrical current to the shape memory material 166, it is resistively heated causing a phase change and a corresponding change in shape. Upon application of electrical current to the bimetallic material 168, it is resistively heated causing a differential in thermal expansion and a corresponding change in shape. In either case, the material 166/168 is designed such that the change in shape causes constriction of the structure 162 to mechanically activate baroreceptors 30 by compressing or otherwise deforming the baroreceptors 30 and/or the vascular wall 40.

Upon removal of the electrical current, the material 166/168 cools and the structure 162 returns to its relaxed geometry such that the baroreceptors 30 and/or the vascular wall 40 return to their nominal state. Thus, by selectively compressing the structure 162, the baroreceptors 30 adjacent thereto may be selectively activated.

Figure 8B:
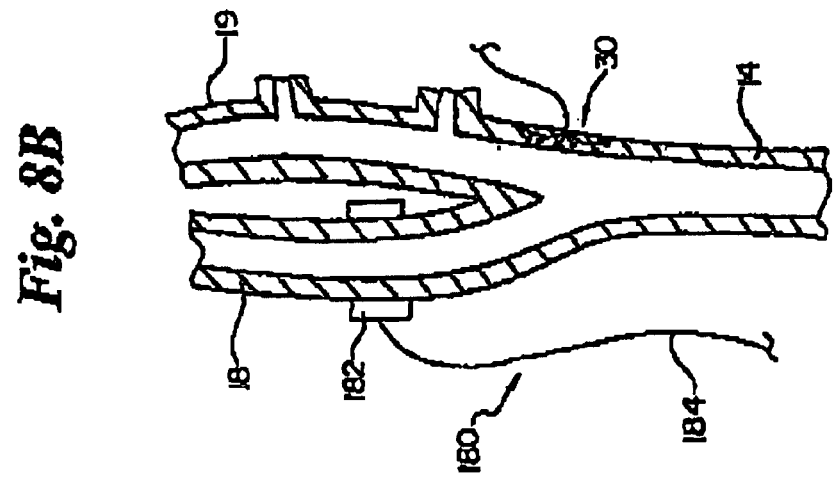
FIGS. 8A and 8B are schematic illustrations of a baroreceptor activation device in the form of an external flow regulator which artificially creates back pressure to induce a baroreceptor signal in accordance with an embodiment of the present invention.
Figure 8A:
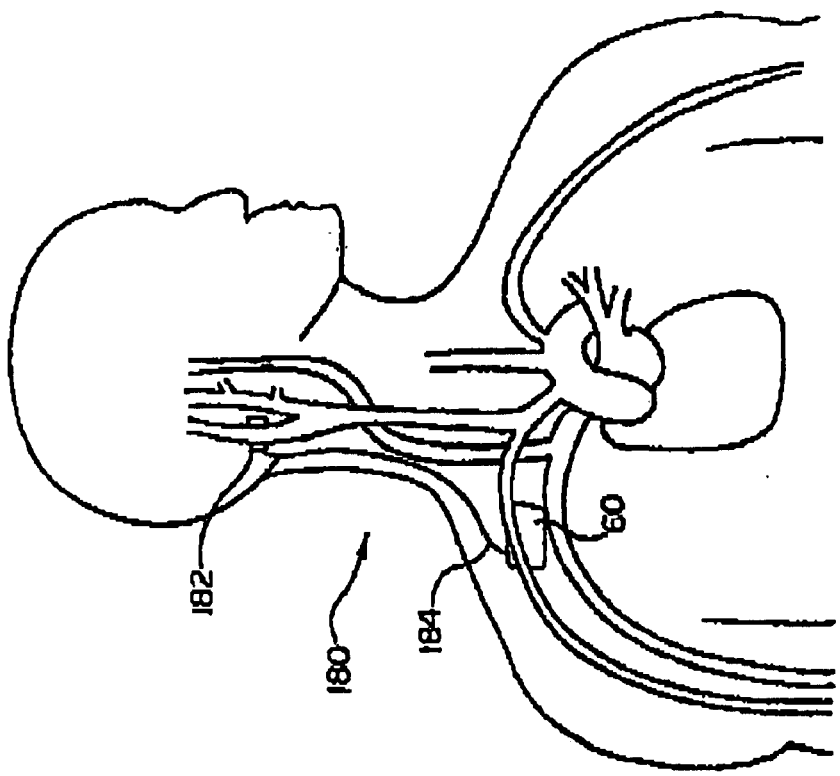

Refer now to FIGS. 8A and 8B which show schematic illustrations of a baroreceptor activation device 180 in the form of an extravascular flow regulator which artificially creates back pressure adjacent the baroreceptors 30. The flow regulator device 180 includes an external compression device 182, which may comprise any of the external compression devices described with reference to FIGS. 5A and 5B. The external compression device 182 is operably connected to the driver 66 of the control system 60 by way of cable 184, which may comprise a fluid line or electrical lead, depending on the type of external compression device 182 utilized. The external compression device 182 is disposed about the vascular wall distal of the baroreceptors 30. For example, the external compression device 182 may be located in the distal portions of the external or internal carotid arteries 18/19 to create back pressure adjacent to the baroreceptors 30 in the carotid sinus region 20. Alternatively, the external compression device 182 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

Upon actuation of the external compression device 182, the vascular wall is constricted thereby reducing the size of the vascular lumen therein. By reducing the size of the vascular lumen, pressure proximal of the external compression device 182 is increased thereby expanding the vascular wall. Thus, by selectively activating the external compression device 182 to constrict the vascular lumen and create back pressure, the baroreceptors 30 may be selectively activated.

Figure 9B:
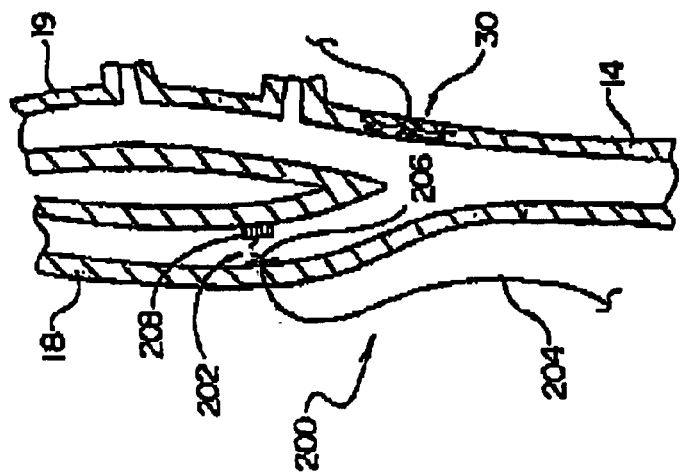
FIGS. 9A and 9B are schematic illustrations of a baroreceptor activation device in the form of an internal flow regulator which artificially creates back pressure to induce a baroreceptor signal in accordance with an embodiment of the present invention.
Figure 9A:
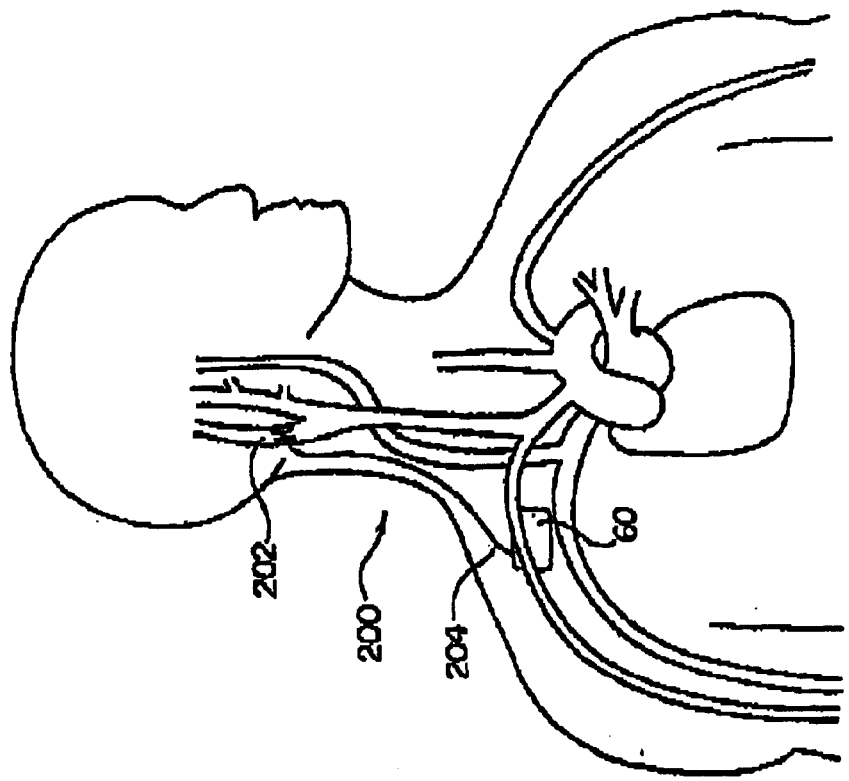

Refer now to FIGS. 9A and 9B which show schematic illustrations of a baroreceptor activation device 200 in the form of an intravascular flow regular which artificially creates back pressure adjacent the baroreceptors 30. The intravascular flow regulator device 200 is substantially similar in function and use as extravascular flow regulator 180 described with reference to FIGS. 8A and 8B, except that the intravascular flow regulator device 200 is disposed in the vascular lumen.

Intravascular flow regulator 200 includes an internal valve 202 to at least partially close the vascular lumen distal of the baroreceptors 30. By at least partially closing the vascular lumen distal of the baroreceptors 30, back pressure is created proximal of the internal valve 202 such that the vascular wall expands to activate the baroreceptors 30. The internal valve 202 may be positioned at any of the locations described with reference to the external compression device 182, except that the internal valve 202 is placed within the vascular lumen. Specifically, the internal compression device 202 may be located in the distal portions of the external or internal carotid arteries 18/19 to create back pressure adjacent to the baroreceptors 30 in the carotid sinus region 20. Alternatively, the internal compression device 202 may be located in the right subclavian artery 13, the right common carotid artery 14, the left common carotid artery 15, the left subclavian artery 16, or the brachiocephalic artery 22 to create back pressure adjacent the baroreceptors 30 in the aortic arch 12.

The internal valve 202 is operably coupled to the driver 66 of the control system 60 by way of electrical lead 204. The control system 60 may selectively open, close or change the flow resistance of the valve 202 as described in more detail hereinafter. The internal valve 202 may include valve leaflets 206 (bi-leaflet or tri-leaflet) which rotate inside housing 208 about an axis between an open position and a closed position. The closed position may be completely closed or partially closed, depending on the desired amount of back pressure to be created. The opening and closing of the internal valve 202 may be selectively controlled by altering the resistance of leaflet 206 rotation or by altering the opening force of the leaflets 206. The resistance of rotation of the leaflets 206 may be altered utilizing electromagnetically actuated metallic bearings carried by the housing 208. The opening force of the leaflets 206 may be altered by utilizing electromagnetic coils in each of the leaflets to selectively magnetize the leaflets such that they either repel or attract each other, thereby facilitating valve opening and closing, respectively.

A wide variety of intravascular flow regulators may be used in place of internal valve 202. For example, internal inflatable balloon devices as disclosed in U.S. Pat. No. 4,682,583 to Burton et al. and U.S. Pat. No. 5,634,878 to Grundei et al., the entire disclosures of which is hereby incorporated by reference, may be adapted for use in place of valve 202. Such inflatable balloon devices may be operated in a similar manner as the inflatable cuff 122 described with reference to FIG. 5. Specifically, in this embodiment, the driver 66 would comprises a pressure/vacuum source (i.e., an inflation device) which selectively inflates and deflates the internal balloon. Upon inflation, the balloon expands to partially occlude blood flow and create back pressure to mechanically activate baroreceptors 30 by stretching or otherwise deforming them and/or the vascular wall 40. Upon deflation, the internal balloon returns to its normal profile such that flow is not hindered and back pressure is eliminated. Thus, by selectively inflating the internal balloon, the baroreceptors 30 proximal thereof may be selectively activated by creating back pressure.

Figure 10B:
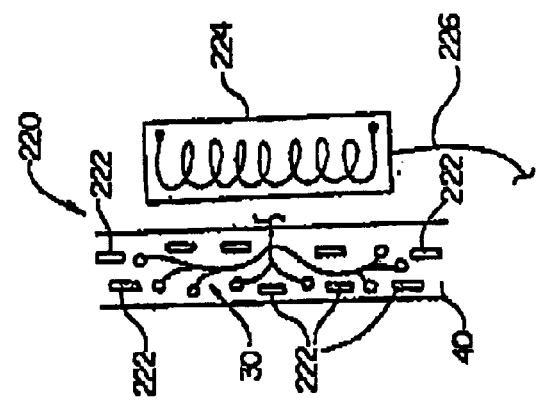
FIGS. 10A and 10B are schematic illustrations of a baroreceptor activation device in the form of a magnetic device which mechanically induces a baroreceptor signal in accordance with an embodiment of the present invention.
Figure 10A:
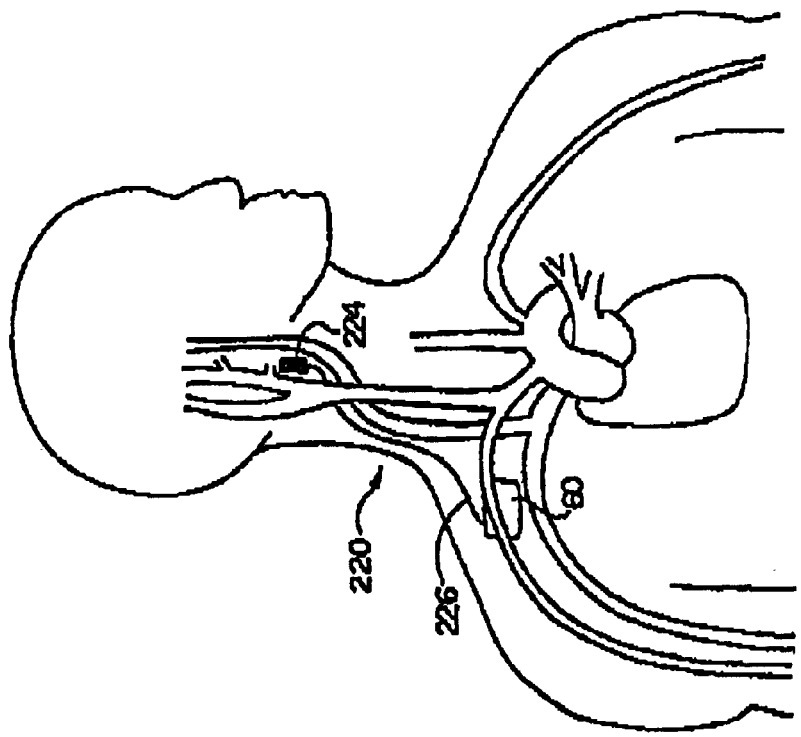

Refer now to FIGS. 10A and 10B which show schematic illustrations of a baroreceptor activation device 220 in the form of magnetic particles 222 disposed in the vascular wall 40. The magnetic particles 222 may comprise magnetically responsive materials (i.e., ferrous based materials) and may be magnetically neutral or magnetically active. Preferably, the magnetic particles 222 comprise permanent magnets having an elongate cylinder shape with north and south poles to strongly respond to magnetic fields. The magnetic particles 222 are actuated by an electromagnetic coil 224 which is operably coupled to the driver 66 of the control system 60 by way of an electrical cable 226. The electromagnetic coil 224 may be implanted as shown, or located outside the body, in which case the driver 66 and the remainder of the control system 60 would also be located outside the body. By selectively activating the electromagnetic coil 224 to create a magnetic field, the magnetic particles 222 may be repelled, attracted or rotated. Alternatively, the magnetic field created by the electromagnetic coil 224 may be alternated such that the magnetic particles 222 vibrate within the vascular wall 40. When the magnetic particles are repelled, attracted, rotated, vibrated or otherwise moved by the magnetic field created by the electromagnetic coil 224, the baroreceptors 30 are mechanically activated.

The electromagnetic coil 224 is preferably placed as close as possible to the magnetic particles 222 in the vascular wall 40, and may be placed intravascularly, extravascularly, or in any of the alternative locations discussed with reference to inductor shown in FIGS. 14–16. The magnetic particles 222 may be implanted in the vascular wall 40 by injecting a ferro-fluid or a ferro-particle suspension into the vascular wall adjacent to the baroreceptors 30. To increase biocompatibility, the particles 222 may be coated with a ceramic, polymeric or other inert material. Injection of the fluid carrying the magnetic particles 222 is preferably performed percutaneously.

Refer now to FIGS. 11A and 11B which show schematic illustrations of a baroreceptor activation device 240 in the form of one or more transducers 242. Preferably, the transducers 242 comprise an array surrounding the vascular wall. The transducers 242 may be intravascularly or extravascularly positioned adjacent to the baroreceptors 30. In this embodiment, the transducers 242 comprise devices which convert electrical signals into some physical phenomena, such as mechanical vibration or acoustic waves. The electrical signals are provided to the transducers 242 by way of electrical cables 244 which are connected to the driver 66 of the control system 60. By selectively activating the transducers 242 to create a physical phenomena, the baroreceptors 30 may be mechanically activated.

The transducers 242 may comprise an acoustic transmitter which transmits sonic or ultrasonic sound waves into the vascular wall 40 to activate the baroreceptors 30. Alternatively, the transducers 242 may comprise a piezoelectric material which vibrates the vascular wall to activate the baroreceptors 30. As a further alternative, the transducers 242 may comprise an artificial muscle which deflects upon application of an electrical signal. An example of an artificial muscle transducer comprises plastic impregnated with a lithium-perchlorate electrolyte disposed between sheets of polypyrrole, a conductive polymer. Such plastic muscles may be electrically activated to cause deflection in different directions depending on the polarity of the applied current.

Figure 12B:
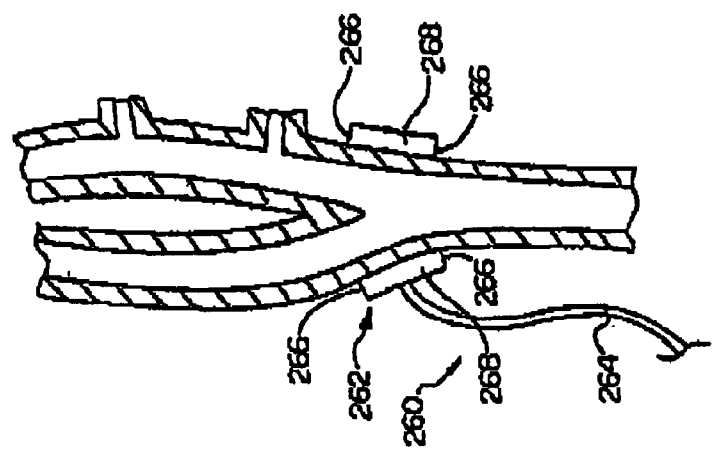
FIGS. 12A and 12B are schematic illustrations of a baroreceptor activation device in the form of a fluid delivery device which may be used to deliver an agent which chemically or biologically induces a baroreceptor signal in accordance with an embodiment of the present invention.
Figure 12A:
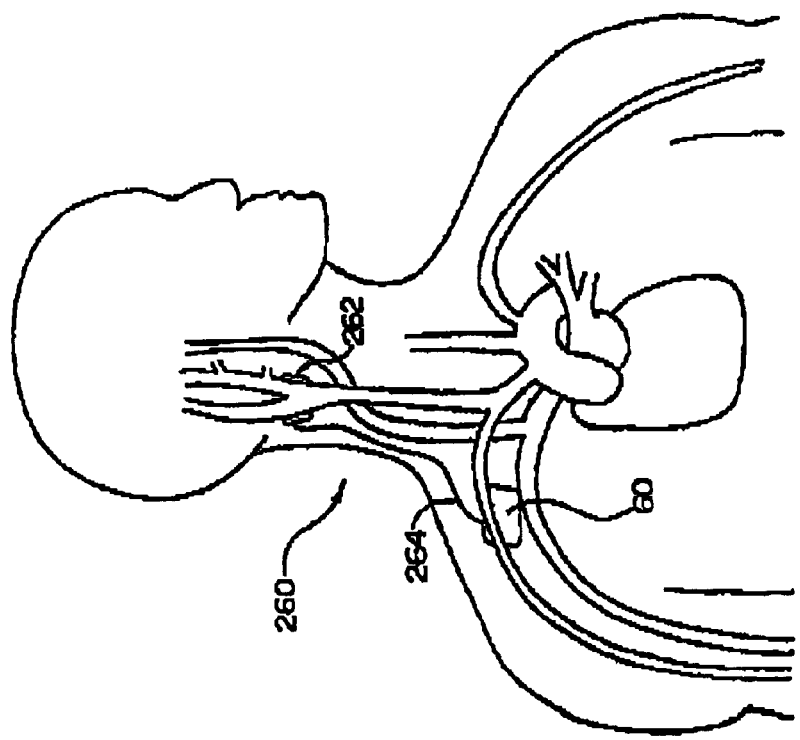

Refer now to FIGS. 12A and 12B which show schematic illustrations of a baroreceptor activation device 260 in the form of a local fluid delivery device 262 suitable for delivering a chemical or biological fluid agent to the vascular wall adjacent the baroreceptors 30. The local fluid delivery device 262 may be located intravascularly, extravascularly, or intramurally. For purposes of illustration only, the local fluid delivery device 262 is positioned extravascularly.

The local fluid delivery device 262 may include proximal and distal seals 266 which retain the fluid agent disposed in the lumen or cavity 268 adjacent to vascular wall. Preferably, the local fluid delivery device 262 completely surrounds the vascular wall 40 to maintain an effective seal. Those skilled in the art will recognize that the local fluid delivery device 262 may comprise a wide variety of implantable drug delivery devices or pumps known in the art.

The local fluid delivery device 260 is connected to a fluid line 264 which is connected to the driver 66 of the control system 60. In this embodiment, the driver 66 comprises a pressure/vacuum source and fluid reservoir containing the desired chemical or biological fluid agent. The chemical or biological fluid agent may comprise a wide variety of stimulatory substances. Examples include veratridine, bradykinin, prostaglandins, and related substances. Such stimulatory substances activate the baroreceptors 30 directly or enhance their sensitivity to other stimuli and therefore may be used in combination with the other baroreceptor activation devices described herein. Other examples include growth factors and other agents that modify the function of the baroreceptors 30 or the cells of the vascular tissue surrounding the baroreceptors 30 causing the baroreceptors 30 to be activated or causing alteration of their responsiveness or activation pattern to other stimuli. It is also contemplated that injectable stimulators that are induced remotely, as described in U.S. Pat. No. 6,061,596 which is incorporated herein by reference, may be used with the present invention.

As an alternative, the fluid delivery device 260 may be used to deliver a photochemical that is essentially inert until activated by light to have a stimulatory effect as described above. In this embodiment, the fluid delivery device 260 would include a light source such as a light emitting diode (LED), and the driver 66 of the control system 60 would include a pulse generator for the LED combined with a pressure/vacuum source and fluid reservoir described previously. The photochemical would be delivered with the fluid delivery device 260 as described above, and the photochemical would be activated, deactivated or modulated by activating, deactivating or modulating the LED.

As a further alternative, the fluid delivery device 260 may be used to deliver a warm or hot fluid (e.g. saline) to thermally activate the baroreceptors 30. In this embodiment, the driver 66 of the control system 60 would include a heat generator for heating the fluid, combined with a pressure/vacuum source and fluid reservoir described previously. The hot or warm fluid would be delivered and preferably circulated with the fluid delivery device 260 as described above, and the temperature of the fluid would be controlled by the driver 66.

Refer now to FIGS. 13A and 13B which show schematic illustrations of a baroreceptor activation device 280 in the form of an intravascular electrically conductive structure or electrode 282. The electrode structure 282 may comprise a self-expanding or balloon expandable coil, braid or other stent-like structure disposed in the vascular lumen. The electrode structure 282 may serve the dual purpose of maintaining lumen patency while also delivering electrical stimuli. To this end, the electrode structure 282 may be implanted utilizing conventional intravascular stent and filter delivery techniques. Preferably, the electrode structure 282 comprises a geometry which allows blood perfusion therethrough. The electrode structure 282 comprises electrically conductive material which may be selectively insulated to establish contact with the inside surface of the vascular wall 40 at desired locations, and limit extraneous electrical contact with blood flowing through the vessel and other tissues.

The electrode structure 282 is connected to electric lead 284 which is connected to the driver 66 of the control system 60. The driver 66, in this embodiment, may comprise a power amplifier, pulse generator or the like to selectively deliver electrical control signals to structure 282. As mentioned previously, the electrical control signal generated by the driver 66 may be continuous, periodic, episodic or a combination thereof, as dictated by an algorithm contained in memory 62 of the control system 60. Continuous control signals include a constant pulse, a constant train of pulses, a triggered pulse and a triggered train of pulses. Periodic control signals include each of the continuous control signals described above which have a designated start time and a designated duration. Episodic control signals include each of the continuous control signals described above which are triggered by an episode.

By selectively activating, deactivating or otherwise modulating the electrical control signal transmitted to the electrode structure 282, electrical energy may be delivered to the vascular wall to activate the baroreceptors 30. As discussed previously, activation of the baroreceptors 30 may occur directly or indirectly. In particular, the electrical signal delivered to the vascular wall 40 by the electrode structure 282 may cause the vascular wall to stretch or otherwise deform thereby indirectly activating the baroreceptors 30 disposed therein. Alternatively, the electrical signals delivered to the vascular wall by the electrode structure 282 may directly activate the baroreceptors 30 by changing the electrical potential across the baroreceptors 30. In either case, the electrical signal is delivered to the vascular wall 40 immediately adjacent to the baroreceptors 30. It is also contemplated that the electrode structure 282 may delivery thermal energy by utilizing a semi-conductive material having a higher resistance such that the electrode structure 282 resistively generates heat upon application of electrical energy.

Figure 18B:
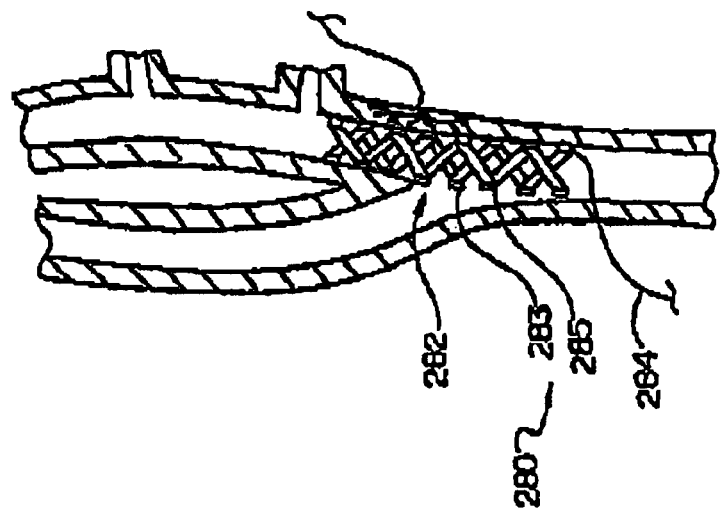
FIGS. 18A and 18B are schematic illustrations of a baroreceptor activation device in the form of an internal bipolar conductive structure which electrically or thermally induces a baroreceptor signal in accordance with an embodiment of the present invention.
Figure 18A:
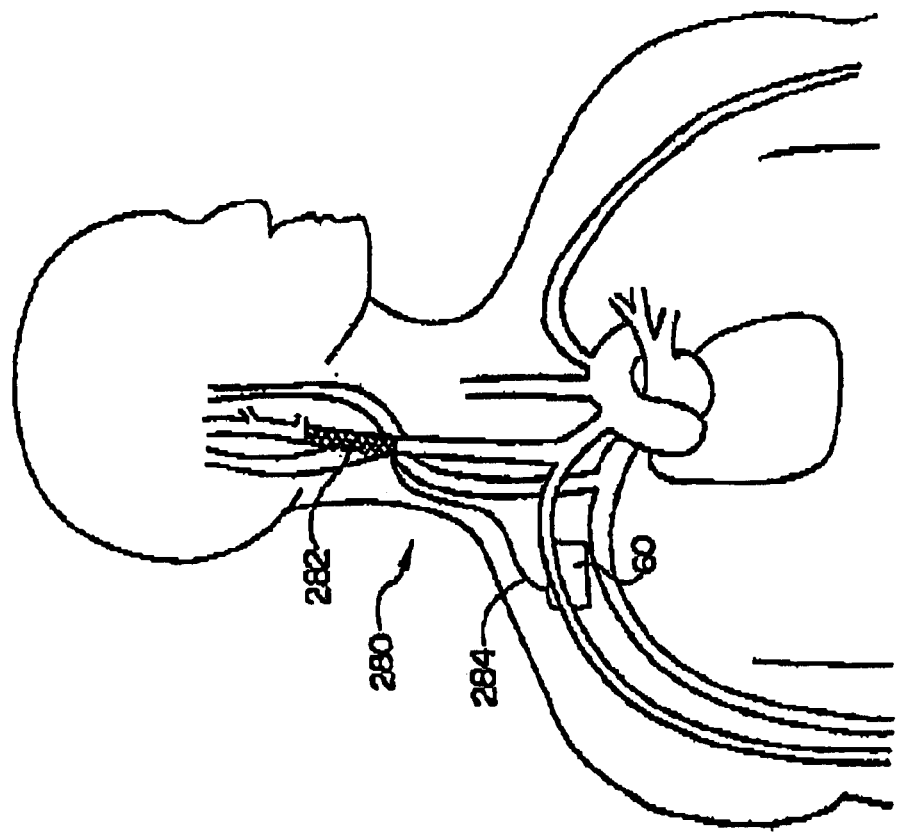

Various alternative embodiments are contemplated for the electrode structure 282, including its design, implanted location, and method of electrical activation. For example, the electrode structure 282 may be unipolar as shown in FIGS. 13A and 13B using the surrounding tissue as ground, or bipolar using leads connected to either end of the structure 282 as shown in FIGS. 18A and 18B. In the embodiment of FIGS. 18A and 18B, the electrode structure 282 includes two or more individual electrically conductive members 283/285 which are electrically isolated at their respective cross-over points utilizing insulative materials. Each of the members 283/285 is connected to a separate conductor contained within the electrical lead 284. Alternatively, an array of bipoles may be used as described in more detail with reference to FIG. 21. As a further alternative, a multipolar arrangement may be used wherein three or more electrically conductive members are included in the structure 282. For example, a tripolar arrangement may be provided by one electrically conductive member having a polarity disposed between two electrically conductive members having the opposite polarity.

Figure 21B:
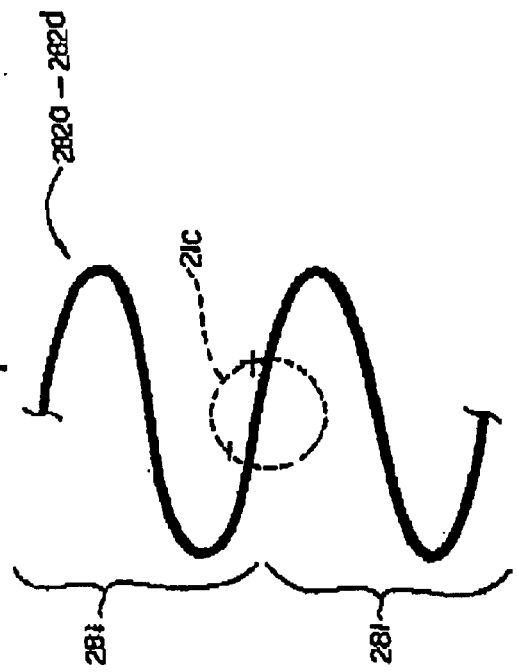
FIGS. 21A–21C are schematic illustrations of a preferred embodiment of an inductively activated electrically conductive structure.
Figure 21C:
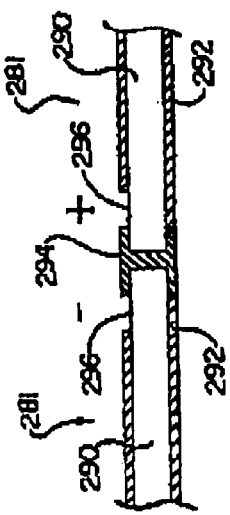
Figure 21A:
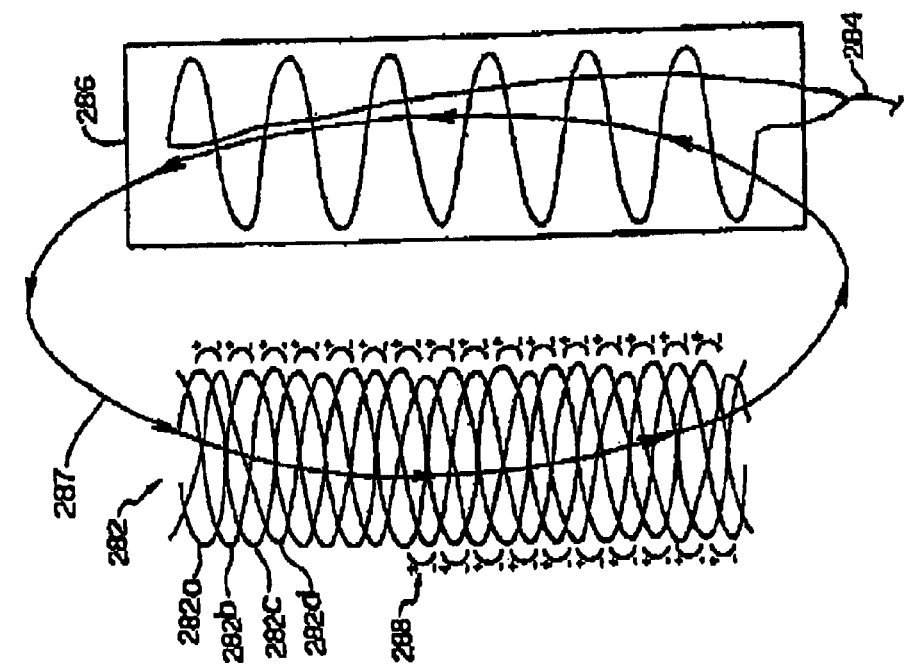

In terms of electrical activation, the electrical signals may be directly delivered to the electrode structure 282 as described with reference to FIGS. 13A and 13B, or indirectly delivered utilizing an inductor as illustrated in FIGS. 14–16 and 21. The embodiments of FIGS. 14–16 and 21 utilize an inductor 286 which is operably connected to the driver 66 of the control system 60 by way of electrical lead 284. The inductor 286 comprises an electrical winding which creates a magnetic field 287 (as seen in FIG. 21) around the electrode structure 282. The magnetic field 287 may be alternated by alternating the direction of current flow through the inductor 286. Accordingly, the inductor 286 may be utilized to create current flow in the electrode structure 282 to thereby deliver electrical signals to the vascular wall 40 to directly or indirectly activate the baroreceptors 30. In all embodiments, the inductor 286 may be covered with an electrically insulative material to eliminate direct electrical stimulation of tissues surrounding the inductor 286. A preferred embodiment of an inductively activated electrode structure 282 is described in more detail with reference to FIGS. 21A–21C.

The embodiments of FIGS. 13–16 may be modified to form a cathode/anode arrangement. Specifically, the electrical inductor 286 would be connected to the driver 66 as shown in FIGS. 14–16 and the electrode structure 282 would be connected to the driver 66 as shown in FIG. 13. With this arrangement, the electrode structure 282 and the inductor 286 may be any suitable geometry and need not be coiled for purposes of induction. The electrode structure 282 and the inductor 286 would comprise a cathode/anode or anode/cathode pair. For example, when activated, the cathode 282 may generate a primary stream of electrons which travel through the inter-electrode space (i.e., vascular tissue and baroreceptors 30) to the anode 286. The cathode is preferably cold, as opposed to thermionic, during electron emission. The electrons may be used to electrically or thermally activate the baroreceptors 30 as discussed previously.

Figure 15B:
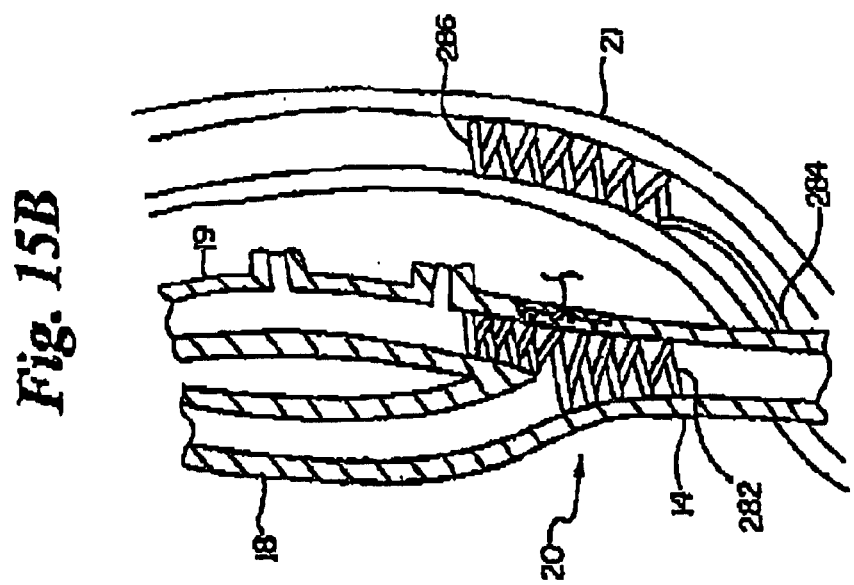
FIGS. 15A and 15B are schematic illustrations of a baroreceptor activation device in the form of an internal conductive structure, activated by an internal inductor located in an adjacent vessel, which electrically or thermally induces a baroreceptor signal in accordance with an embodiment of the present invention.
Figure 15A:
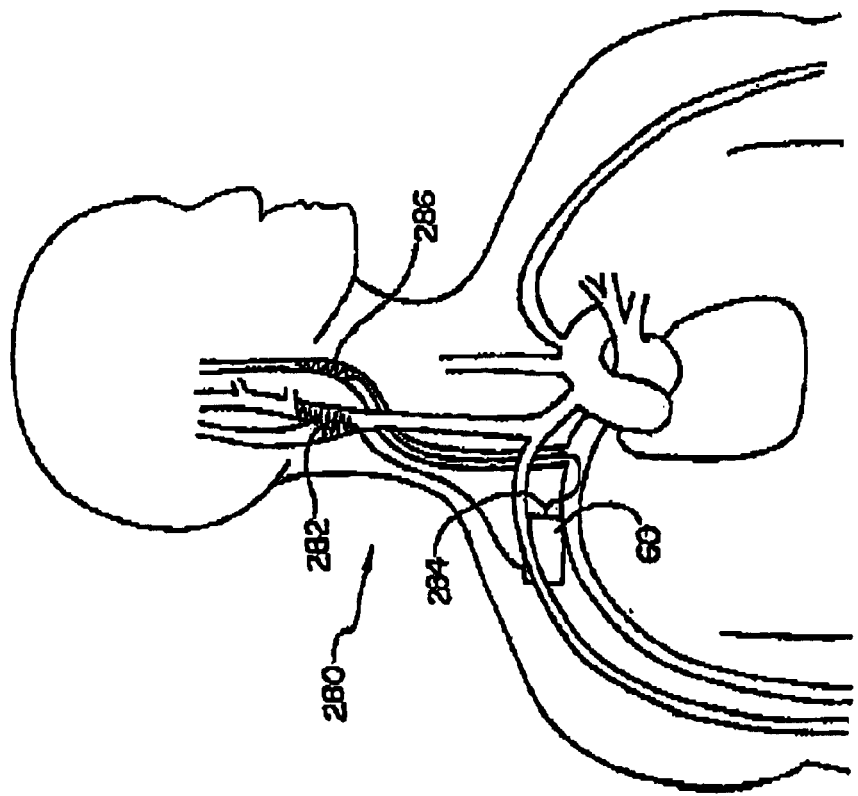

The electrical inductor 286 is preferably disposed as close as possible to the electrode structure 282. For example, the electrical inductor 286 may be disposed adjacent the vascular wall as illustrated in FIGS. 14A and 14B. Alternatively, the inductor 286 may be disposed in an adjacent vessel as illustrated in FIGS. 15A and 15B. If the electrode structure 282 is disposed in the carotid sinus 20, for example, the inductor 286 may be disposed in the internal jugular vein 21 as illustrated in FIGS. 15A and 15B. In the embodiment of FIGS. 15A and 15B, the electrical inductor 286 may comprise a similar structure as the electrode structure 282. As a further alternative, the electrical inductor 286 may be disposed outside the patient's body, but as close as possible to the electrode structure 282. If the electrode structure 282 is disposed in the carotid sinus 20, for example, the electrical inductor 286 may be disposed on the right or left side of the neck of the patient as illustrated in FIGS. 16A and 16B. In the embodiment of FIGS. 16A and 16B, wherein the electrical inductor 286 is disposed outside the patient's body, the control system 60 may also be disposed outside the patient's body.

In terms of implant location, the electrode structure 282 may be intravascularly disposed as described with reference to FIGS. 13A and 13B, or extravascularly disposed as described with reference to FIGS. 17A and 17B, which show schematic illustrations of a baroreceptor activation device 300 in the form of an extravascular electrically conductive structure or electrode 302. Except as described herein, the extravascular electrode structure 302 is the same in design, function, and use as the intravascular electrode structure 282. The electrode structure 302 may comprise a coil, braid or other structure capable of surrounding the vascular wall. Alternatively, the electrode structure 302 may comprise one or more electrode patches distributed around the outside surface of the vascular wall. Because the electrode structure 302 is disposed on the outside surface of the vascular wall, intravascular delivery techniques may not be practical, but minimally invasive surgical techniques will suffice. The extravascular electrode structure 302 may receive electrical signals directly from the driver 66 of the control system 60 by way of electrical lead 304, or indirectly by utilizing an inductor (not shown) as described with reference to FIGS. 14–16.

Figure 19B:
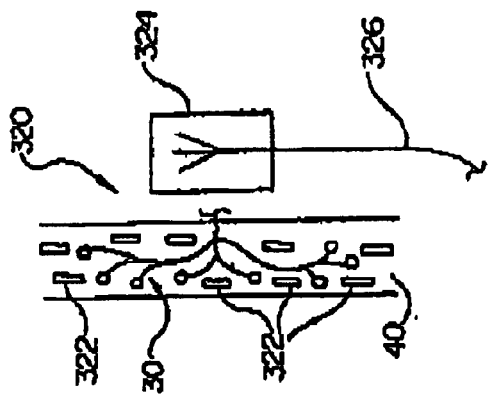
FIGS. 19A and 19B are schematic illustrations of a baroreceptor activation device in the form of an electromagnetic field responsive device which electrically or thermally induces a baroreceptor signal in accordance with an embodiment of the present invention.
Figure 19A:
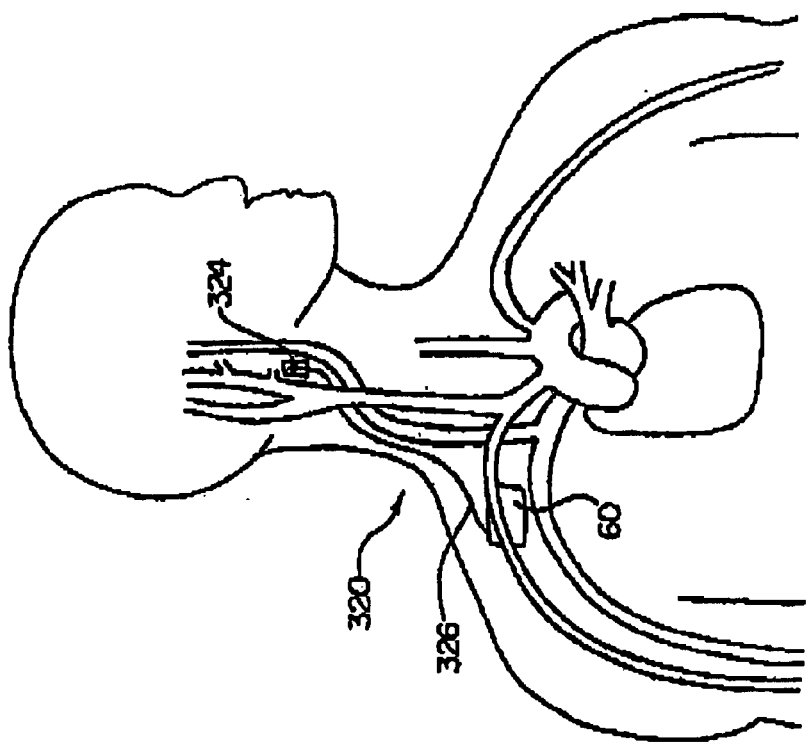

Refer now to FIGS. 19A and 19B which show schematic illustrations of a baroreceptor activation device 320 in the form of electrically conductive particles 322 disposed in the vascular wall. This embodiment is substantially the same as the embodiments described with reference to FIGS. 13–18, except that the electrically conductive particles 322 are disposed within the vascular wall, as opposed to the electrically conductive structures 282/302 which are disposed on either side of the vascular wall. In addition, this embodiment is similar to the embodiment described with reference to FIG. 10, except that the electrically conductive particles 322 are not necessarily magnetic as with magnetic particles 222, and the electrically conductive particles 322 are driven by an electromagnetic filed rather than by a magnetic field.

In this embodiment, the driver 66 of the control system 60 comprises an electromagnetic transmitter such as an radiofrequency or microwave transmitter. Electromagnetic radiation is created by the transmitter 66 which is operably coupled to an antenna 324 by way of electrical lead 326. Electromagnetic waves are emitted by the antenna 324 and received by the electrically conductive particles 322 disposed in the vascular wall 40. Electromagnetic energy creates oscillating current flow within the electrically conductive particles 322, and depending on the intensity of the electromagnetic radiation and the resistivity of the conductive particles 322, may cause the electrical particles 322 to generate heat. The electrical or thermal energy generated by the electrically conductive particles 322 may directly activate the baroreceptors 30, or indirectly activate the baroreceptors 30 by way of the surrounding vascular wall tissue.

The electromagnetic radiation transmitter 66 and antenna 324 may be disposed in the patient's body, with the antenna 324 disposed adjacent to the conductive particles in the vascular wall 40 as illustrated in FIGS. 19A and 19B. Alternatively, the antenna 324 may be disposed in any of the positions described with reference to the electrical inductor shown in FIGS. 14–16. It is also contemplated that the electromagnetic radiation transmitter 66 and antenna 324 may be utilized in combination with the intravascular and extravascular electrically conductive structures 282/302 described with reference to FIGS. 13–18 to generate thermal energy on either side of the vascular wall.

As an alternative, the electromagnetic radiation transmitter 66 and antenna 324 may be used without the electrically conductive particles 322. Specifically, the electromagnetic radiation transmitter 66 and antenna 324 may be used to deliver electromagnetic radiation (e.g., RF, microwave) directly to the baroreceptors 30 or the tissue adjacent thereto to cause localized heating, thereby thermally inducing a baroreceptor 30 signal.

Figure 20B:
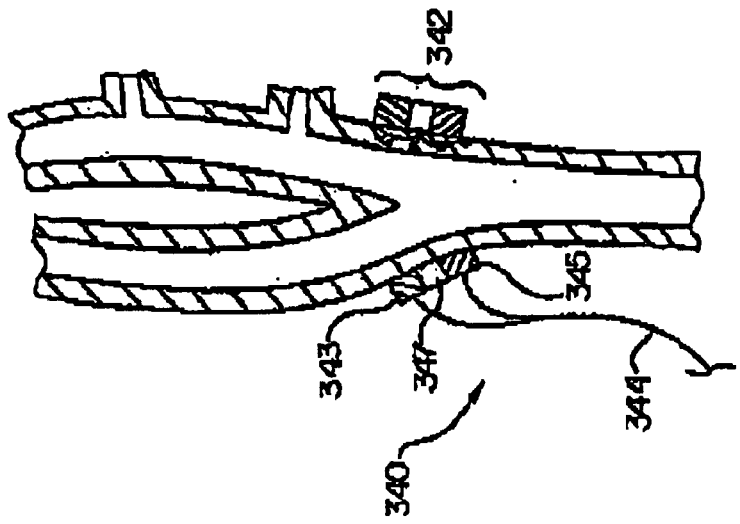
FIGS. 20A and 20B are schematic illustrations of a baroreceptor activation device in the form of an external Peltier device which thermally induces a baroreceptor signal in accordance with an embodiment of the present invention.
Figure 20A:
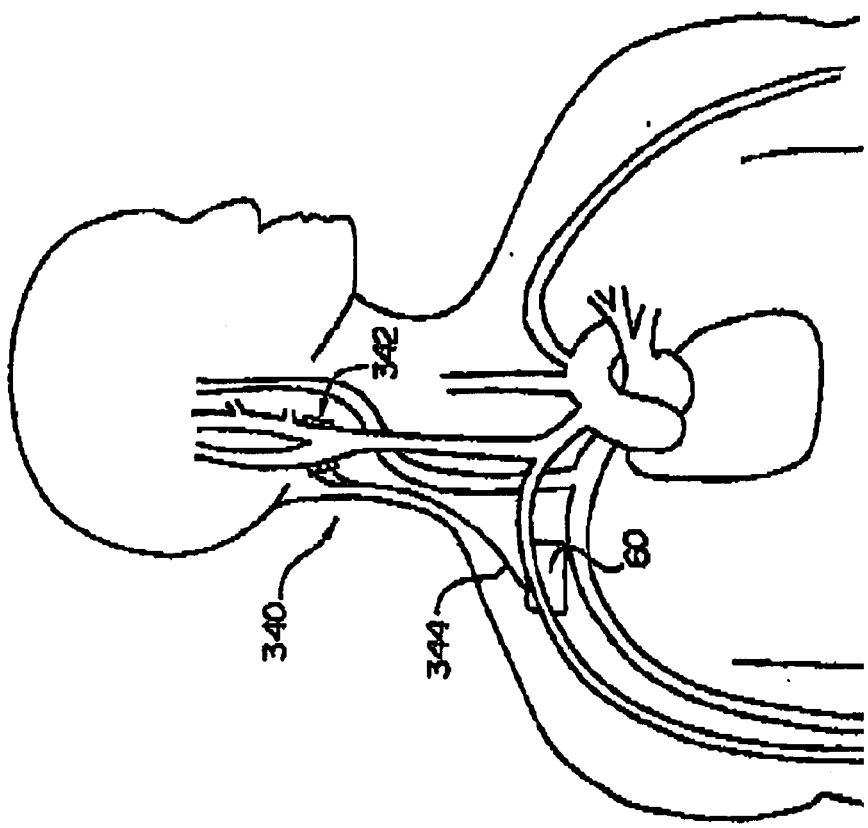

Refer now to FIGS. 20A and 20B which show schematic illustrations of a baroreceptor activation device 340 in the form of a Peltier effect device 342. The Peltier effect device 342 may be extravascularly positioned as illustrated, or may be intravascularly positioned similar to an intravascular stent or filter. The Peltier effect device 342 is operably connected to the driver 66 of the control system 60 by way of electrical lead 344. The Peltier effect device 342 includes two dissimilar metals or semiconductors 343/345 separated by a thermal transfer junction 347. In this particular embodiment, the driver 66 comprises a power source which delivers electrical energy to the dissimilar metals or semiconductors 343/345 to create current flow across the thermal junction 347.

When current is delivered in an appropriate direction, a cooling effect is created at the thermal junction 347. There is also a heating effect created at the junction between the individual leads 344 connected to the dissimilar metals or semiconductors 343/345. This heating effect, which is proportional to the cooling effect, may be utilized to activate the baroreceptors 30 by positioning the junction between the electrical leads 344 and the dissimilar metals or semiconductors 343/345 adjacent to the vascular wall 40.

Refer now to FIGS. 21A–21C which show schematic illustrations of a preferred embodiment of an inductively activated electrode structure 282 for use with the embodiments described with reference to FIGS. 14–16. In this embodiment, current flow in the electrode structure 282 is induced by a magnetic field 287 created by an inductor 286 which is operably coupled to the driver 66 of the control system 60 by way of electrical cable 284. The electrode structure 282 preferably comprises a multi-filar self-expanding braid structure including a plurality of individual members 282a, 282b, 282c and 282d. However, the electrode structure 282 may simply comprise a single coil for purposes of this embodiment.

Each of the individual coil members 282a–282d comprising the electrode structure 282 consists of a plurality of individual coil turns 281 connected end to end as illustrated in FIGS. 21B and 21C. FIG. 21C is a detailed view of the connection between adjacent coil turns 281 as shown in FIG. 21B. Each coil turn 281 comprises electrically isolated wires or receivers in which a current flow is established when a changing magnetic field 287 is created by the inductor 286. The inductor 286 is preferably covered with an electrically insulative material to eliminate direct electrical stimulation of tissues surrounding the inductor 286. Current flow through each coil turn 281 results in a potential drop 288 between each end of the coil turn 281. With a potential drop defined at each junction between adjacent coil turns 281, a localized current flow cell is created in the vessel wall adjacent each junction. Thus an array or plurality of bipoles are created by the electrode structure 282 and uniformly distributed around the vessel wall. Each coil turn 281 comprises an electrically conductive wire material 290 surrounded by an electrically insulative material 292. The ends of each coil turn 281 are connected by an electrically insulated material 294 such that each coil turn 281 remains electrically isolated. The insulative material 294 mechanically joins but electrically isolates adjacent coil turns 281 such that each turn 281 responds with a similar potential drop 288 when current flow is induced by the changing magnetic field 287 of the inductor 286. An exposed portion 296 is provided at each end of each coil turn 281 to facilitate contact with the vascular wall tissue. Each exposed portion 296 comprises an isolated electrode in contact with the vessel wall. The changing magnetic field 287 of the inductor 286 causes a potential drop in each coil turn 281 thereby creating small current flow cells in the vessel wall corresponding to adjacent exposed regions 296. The creation of multiple small current cells along the inner wall of the blood vessel serves to create a cylindrical zone of relatively high current density such that the baroreceptors 30 are activated. However, the cylindrical current density field quickly reduces to a negligible current density near the outer wall of the vascular wall, which serves to limit extraneous current leakage to minimize or eliminate unwanted activation of extravascular tissues and structures such as nerves or muscles.

To address low blood pressure and other conditions requiring blood pressure augmentation, some of the baroreceptor activation devices described previously may be used to selectively and controllably regulate blood pressure by inhibiting or dampening baroreceptor signals. By selectively and controllably inhibiting or dampening baroreceptor signals, the present invention reduces conditions associated with low blood pressure as described previously. Specifically, the present invention would function to increase the blood pressure and level of sympathetic nervous system activation by inhibiting or dampening the activation of baroreceptors.

This may be accomplished by utilizing mechanical, thermal, electrical and chemical or biological means. Mechanical means may be triggered off the pressure pulse of the heart to mechanically limit deformation of the arterial wall. For example, either of the external compression devices 120/160 described previously may be used to limit deformation of the arterial wall. Alternatively, the external compression device may simply limit diametrical expansion of the vascular wall adjacent the baroreceptors without the need for a trigger or control signal.

Thermal means may be used to cool the baroreceptors 30 and adjacent tissue to reduce the responsiveness of the baroreceptors 30 and thereby dampen baroreceptor signals. Specifically, the baroreceptor 30 signals may be dampened by either directly cooling the baroreceptors 30, to reduce their sensitivity, metabolic activity and function, or by cooling the surrounding vascular wall tissue thereby causing the wall to become less responsive to increases in blood pressure. An example of this approach is to use the cooling effect of the Peltier device 340. Specifically, the thermal transfer junction 347 may be positioned adjacent the vascular wall to provide a cooling effect. The cooling effect may be used to dampen signals generated by the baroreceptors 30. Another example of this approach is to use the fluid delivery device 260 to deliver a cool or cold fluid (e.g. saline). In this embodiment, the driver 66 would include a heat exchanger to cool the fluid and the control system 60 may be used to regulate the temperature of the fluid, thereby regulating the degree of baroreceptor 30 signal dampening.

Electrical means may be used to inhibit baroreceptor 30 activation by, for example, hyperpolarizing cells in or adjacent to the baroreceptors 30. Examples of devices and method of hyperpolarizing cells are disclosed in U.S. Pat. No. 5,814,079 to Kieval, and U.S. Pat. No. 5,800,464 to Kieval, the entire disclosures of which are hereby incorporated by reference. Such electrical means may be implemented using any of the embodiments discussed with reference to FIGS. 13–18 and 21.

Chemical or biological means may be used to reduce the sensitivity of the baroreceptors 30. For example, a substance that reduces baroreceptor sensitivity may be delivered using the fluid delivery device 260 described previously. The desensitizing agent may comprise, for example, tetrodotoxin or other inhibitor of excitable tissues. From the foregoing, it should be apparent to those skilled in the art that the present invention provides a number of devices, systems and methods by which the blood pressure, nervous system activity, and neurohormonal activity may be selectively and controllably regulated by activating baroreceptors or by inhibiting/ dampening baroreceptor signals. Thus, the present invention may be used to increase or decrease blood pressure, sympathetic nervous system activity and neurohormonal activity, as needed to minimize deleterious effects on the heart, vasculature and other organs and tissues.

The baroreceptor activation devices described previously may also be used to provide antiarrhythmic effects. It is well known that the susceptibility of the myocardium to the development of conduction disturbances and malignant cardiac arrhythmias is influenced by the balance between sympathetic and parasympathetic nervous system stimulation to the heart. That is, heightened sympathetic nervous system activation, coupled with decreased parasympathetic stimulation, increases the irritability of the myocardium and likelihood of an arrhythmia. Thus, by decreasing the level of sympathetic nervous system activation and enhancing the level of parasympathetic activation, the devices, systems and methods of the current invention may be used to provide a protective effect against the development of cardiac conduction disturbances.

For each of these applications, it may be desirable to focus the output of the activation device 70 on portions of the carotid sinus 20 that are rich in baroreceptors 30, and minimize the output delivered to portions of the carotid sinus 20 with fewer or no baroreceptors 30. By focusing the output as such, baroreceptor activation may be maximized and the required device output (i.e., the required power or energy output of the baroreceptor activation device 70) may be minimized. In particular, the ratio of baroreceptor activation to device output (A/O) may be maximized. In addition, by focusing the output as such, extraneous tissue activation may be minimized, power consumption (by the device 70) may minimized, and the degradation rate of baroreceptor responsiveness may be minimized.

It has been found that the A/O ratio is a function of the position of the baroreceptor activation device. In particular, it has been found that the A/O ratio varies about the circumference of the carotid artery near the carotid sinus 20, perhaps due to variations in the location or density of baroreceptors. Although described herein with reference to the carotid sinus 20, it is also likely that the A/O ratio varies at all of the anatomical locations which contain baroreceptors as described previously.

In order to position the baroreceptor activation device 70 to maximize the A/O ratio, a mapping technique may be employed. For example, the device 70 may be oriented in two or more different positions and/or at two or more different anatomical locations. More specifically, the output means of the device 70 may be disposed in two or more different positions/locations. The output means generally refers to the structure through which the stimulus is transferred to the tissue surrounding the baroreceptors. In electrical activation embodiments, for example, the output means may comprise electrodes.

At each position/location, the device 70 may be activated to a specified level, and the degree of baroreceptor activation may be observed or measured. The degree of baroreceptor activation may be inferentially determined by measuring changes in heart rate, blood pressure, and/or other physiological parameters indicative of baroreceptor activation. The resulting measurements may be used to generate an A/O ratio for each position/location. The A/O ratios for each location may be graphically plotted to generate a map. The A/O ratios may be compared, and the position/location having the most desirable A/O ratio may be selected for the device 70.

Figure 23:
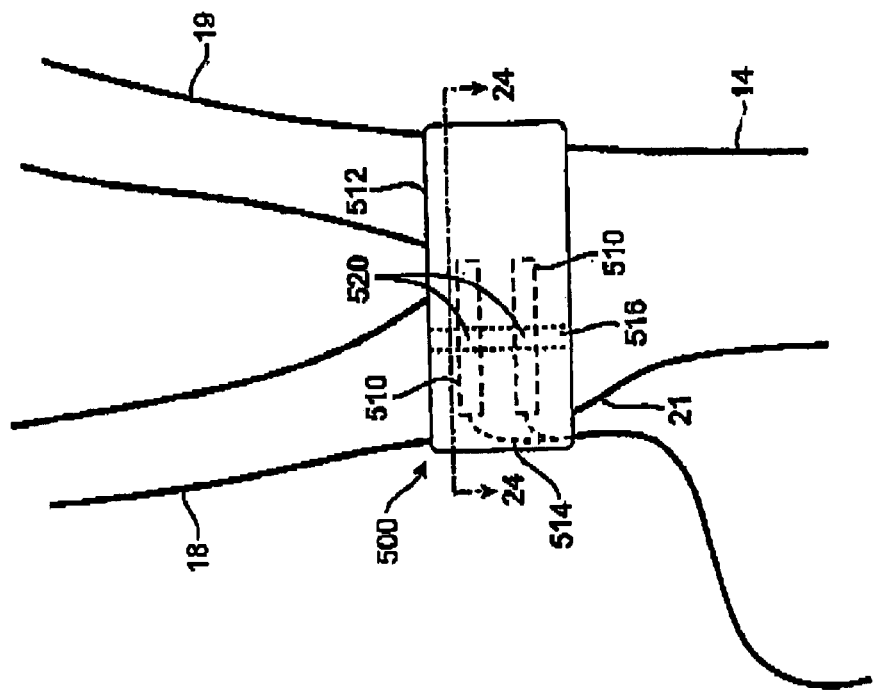
FIG. 23 is a schematic illustration of a baroreceptor activation device disposed a bout the right carotid artery which may be used for mapping baroreceptors therein.
Figure 22:
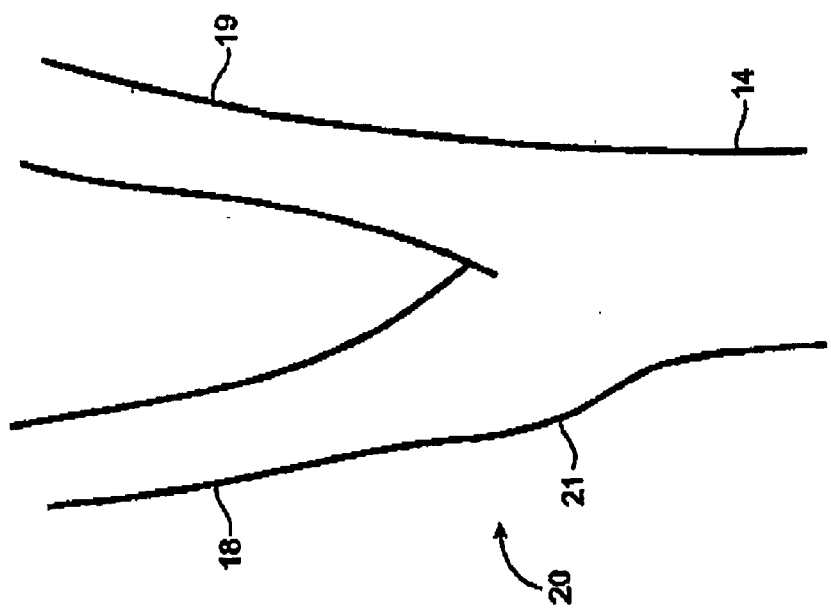
FIG. 22 is a schematic illustration of the right carotid artery showing a bulge in the vascular wall which is a landmark of the carotid sinus.
Figure 24:
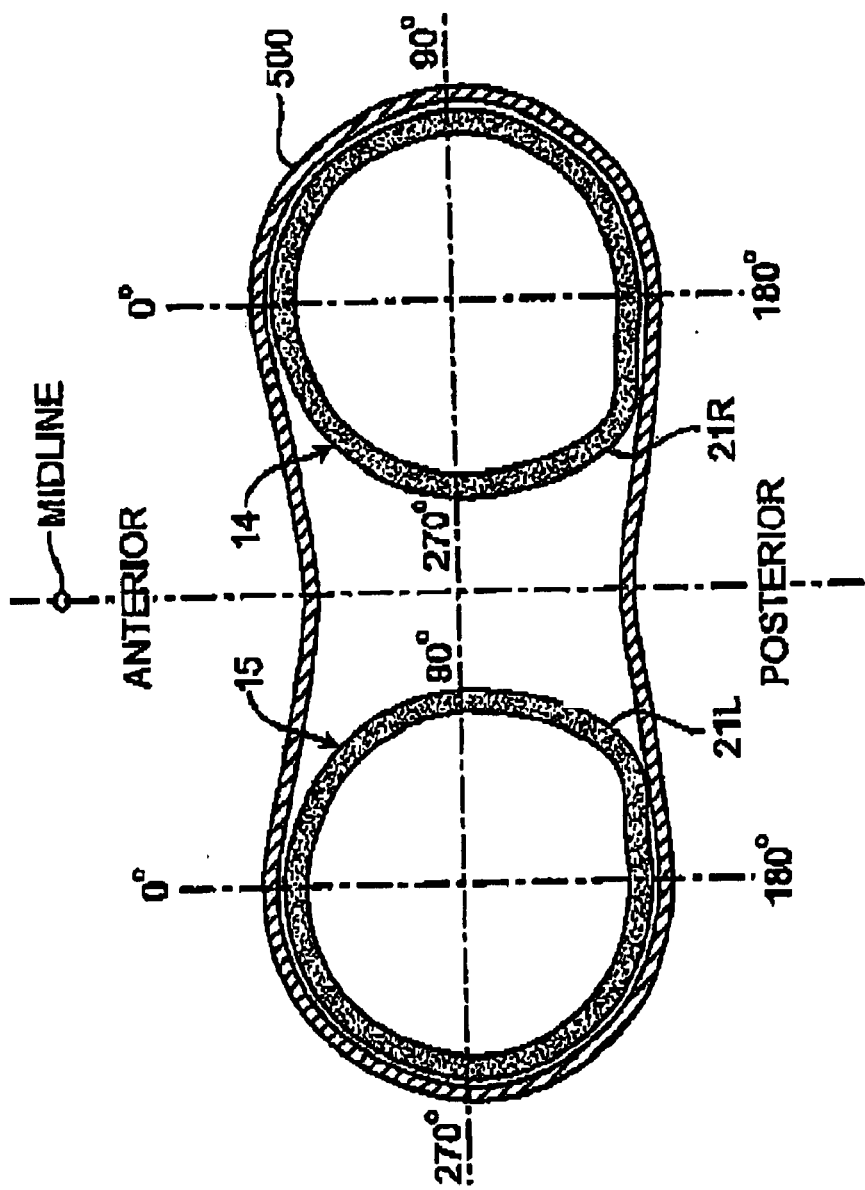
FIG. 24 is a schematic cross-sectional view taken along line 24—24 in FIG. 23, showing a mapping coordinate system for the left and right carotid arteries.

To illustrate this mapping method, reference may be made to FIGS. 22–24. By way of example, not limitation, the mapping method is described with specific reference to the arteries, but the method is equally applicable to all anatomical structures containing baroreceptors. FIG. 22 shows the right carotid arteries including the common 14, internal 18, and external 19 carotid arteries. The carotid sinus 20 may be highlighted by a bulge 21, which typically extends from the common carotid artery 14 to the internal carotid artery 18 near the bifurcation. The carotidسinus 20 contains a significant number of baroreceptors, the number and density of which may vary around the circumference and along the length of the sinus 20. As such, it is desirable to determine the optimal position for the baroreceptor activation device 70, both in terms of circumferential and longitudinal position.

The mapping method described herein is equally applicable to all baroreceptor activation devices 70, regardless of the mode of activation (mechanical, electrical, thermal, chemical, biological, or other means) and regardless of their invivo position (intravascular, extravascular, intramural). By way of example, not limitation, the device 70 is shown in FIG. 23 as an extravascular electrical device 500 having two electrodes 520 which contact the outside wall of the carotid sinus 20 at two different locations. The device 500 includes a molded silicone housing 512. The housing 512 carries two metal strips 510 which are separated by approximately 4 mm and are formed of platinum ribbon (0.040 in. wide by 0.0005 in. thick by 10 mm long). The metal strips 510 are insulated by the housing 512 except at the 1 mm wide exposed area 516. The metal strips 510 in the exposed area 516 define two electrodes 520 that contact the outside surface of the carotid artery. Leads 514 couple the metal strips 510 to cable 502 which is connected to a control system 60 as described previously with reference to FIG. 3.

With the device 500 disposed about the carotid arteries as shown in FIG. 23, the device 500 may be activated to produce an output signal from the electrodes 520, which in turn activates the baroreceptors, as evidenced by a change in heart rate and/or blood pressure. The position and/or location of the electrodes 520 is recorded along with the amount of output (e.g., power) and the corresponding change in the heart rate, blood pressure and/or other physiological parameters indicative of baroreceptor activation. From this information, the A/O ratio may be determined for this particular position/location.

The electrodes 520 of the device 500 are then oriented in a different position (e.g., rotated) and/or placed at a different anatomical location, and the same measurements are made. These steps are repeated to collect the desired amount of data, which may be graphically plotted to generate a map to determine an optimal position/location. The A/O ratios may be compared, and the position/location having the most desirable A/O ratio may be selected for the device 500. As an alternative to device 500, a hand held probe or similar device incorporating electrodes 520 may be used to permit easier manipulation and quicker changes between different locations/positions.

To keep track of different circumferential positions around the carotid arteries, a coordinate system may be used as shown in FIG. 24. FIG. 24 is a schematic cross-sectional view taken along line 24—24 in FIG. 23, showing a mapping coordinate system for the left carotid artery 15 and right carotid artery 14. In this coordinate system, the left carotid artery 15 and right carotid artery 14 are viewed in cross-section looking from the head of the patient toward the feet, with 0° positioned anteriorly and 180° positioned posteriorly. The center or apex of the left bulge 21L which identifies the left carotid sinus 20L is typically located at 110° to 160°. The center or apex of the right bulge 21R which identifies the right carotid sinus 20R is typically located at 200° to 250°. This coordinate system is particularly useful for mapping the circumference of the carotid arteries, in addition to other arteries and tubular organs.

To further illustrate this method, an animal experiment was performed utilizing device 500 on the left and right carotid arteries of an animal. The device 500 was wrapped around the carotid artery near the carotid sinus 20 at the bifurcation of the internal 18 and external 19 carotid arteries, substantially as shown in FIG. 23. Using the coordinate system described with reference to FIG. 24, the center of the bulge 21L of the left carotid sinus 20L for this animal was located at 120°, and the center of the bulge 21R of the right carotid sinus 20R was located at 200°.

Figure 25:
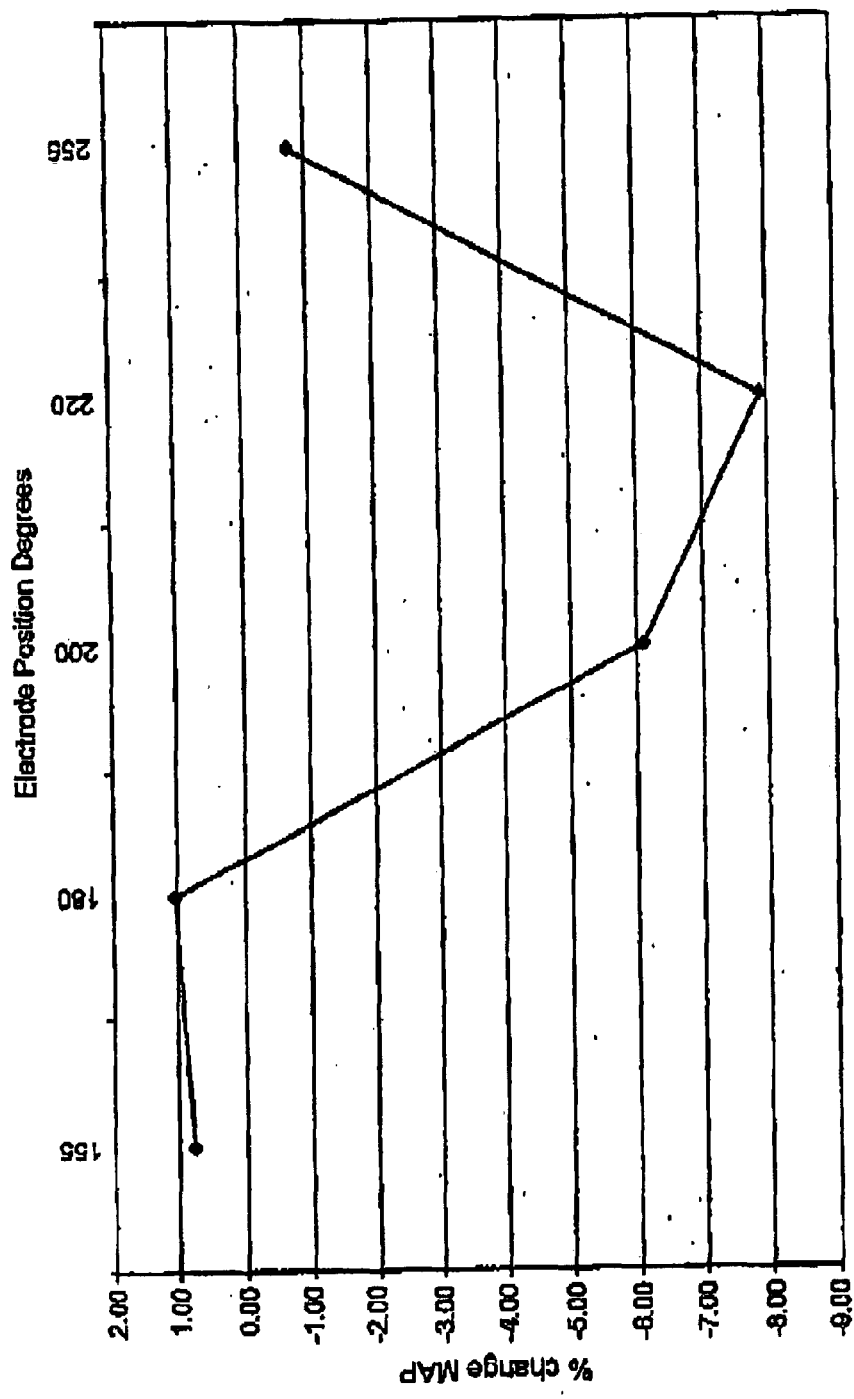
FIGS. 25 and 26 are graphs illustrating the variability of baroreceptor responsiveness around the right and left carotid arteries, respectively.
Figure 26:
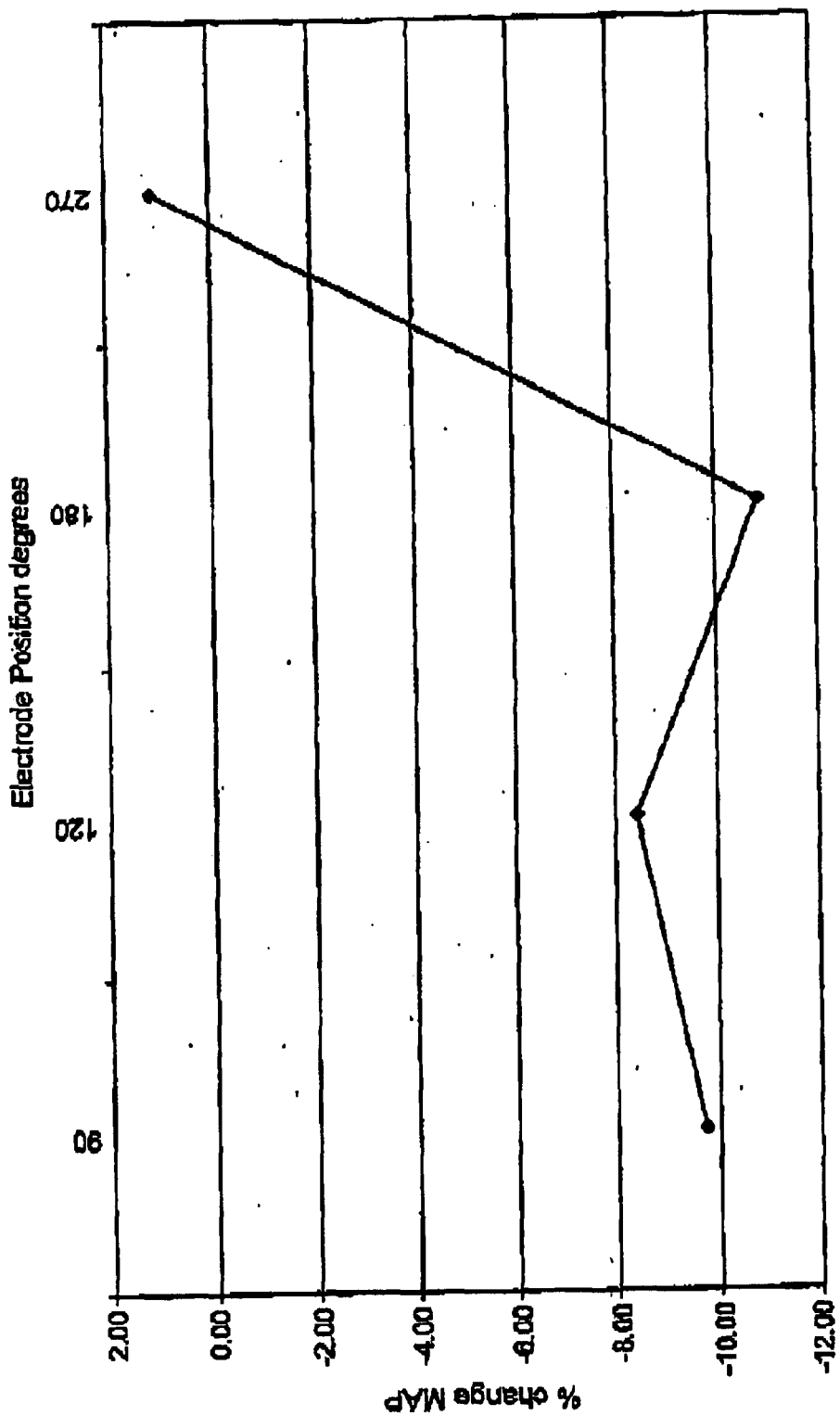

The electrodes 520 were rotated around the left carotid artery at 90°, 120°, 180°, and 270° positions. The electrodes 520 were rotated around the right carotid artery at 155°, 180°, 200°, 220°, and 255° positions. At each position, the electrodes 520 were activated with a 4 volt signal, and the mean arterial pressure (MAP) and heart rate (HR) were measured. The data from the right side is graphically illustrated in FIG. 25, and the data from the left side is graphically illustrated in FIG. 26.

This data suggest that the responsiveness (i.e., the degree of baroreceptor activation) is non-homogenous and unpredictable around the circumference of the carotid arteries. However, from this data, it is possible to locate both hot spots (large A/O ratio) and dead spots (low A/O ratio) around the circumference of the carotid arteries. For example, on the right side, there appears to be a dead zone between 155° and 180°, and a dead spot around 255°. Also on the right side, there appears to be a hot zone between 190° and 220°. On the left side, there appears to be a hot zone from 90° to 180°, and a dead spot near 270°. Thus, there is variability of the A/O ratio around the circumference of the carotid arteries, between the right and left sides, and probably between patients. Because of this variability, the mapping method described herein may be beneficial to positioning the baroreceptor activation device for optimal A/O ratio.

It is also contemplated that the device 500 may have many individually controllable electrodes 520 disposed around a large area of the carotid sinus (e.g., around the entire circumference). Such a device is disclosed in co-pending patent application Ser. No. 09/963,777, filed on even date herewith, entitled ELECTRODE DESIGNS AND METHODS OF USE FOR CARDIOVASCULAR REFLEX CONTROL DEVICES, the entire disclosure of which is hereby incorporated by reference. The electrodes 520 may be individually activated, and the corresponding baroreceptor response for each electrode may be determined. The electrodes 520 having the most desirable A/O ratio(s) may then be selected for chronic use. This method negates the need to reposition or relocate the device to find the optimal A/O ratio. This method also enables the electrode selection to be changed after implantation without the need to change the position/location of the device 500 in a subsequent clinical procedure.

Those skilled in the art will recognize that the present invention may be manifested in a variety of forms other than the specific embodiments described and contemplated herein. Accordingly, departures in form and detail may be made without departing from the scope and spirit of the present invention as described in the appended claims.

What is claimed is:

1. A method of inducing a change in the baroreflex system of a patient, the method comprising the steps of:
providing an activation device;
positioning the activation device proximate a baroreceptor at a first location;
activating, deactivating or otherwise modulating the activation device to induce a baroreflex signal;
measuring the degree of baroreflex activation at the first location;
repositioning the activation device proximate a baroreceptor at a second location;
activating, deactivating or otherwise modulating the activation device to induce a baroreflex signal;
measuring the degree of baroreflex activation at the second location;
comparing the degree of baroreflex activation at the first and second locations;
selecting a final location for the activation device based on the comparison;
positioning the activation device proximate a baroreceptor at the final location; and
activating, deactivating or otherwise modulating the activation device to induce a baroreflex signal.

2. A method as in claim 1, wherein the step of measuring the degree of baroreflex activation at the first location comprises measuring blood pressure.

3. A method as in claim 1, wherein the step of measuring the degree of baroreflex activation at the first location comprises measuring heart rate.

4. A method as in claim 1, wherein the step of repositioning the activation device proximate a baroreceptor at the second location comprises rotating the activation device around a carotid artery.

5. A method as in claim 1, wherein the step of repositioning the activation device proximate a baroreceptor at the second location comprises longitudinally displacing the activation device along a carotid artery.

6. A method as in claim 1, wherein the first location is on an artery, and the second location is on the same artery.

7. A method as in claim 1, wherein the first location is on an artery, and the second location is on a different artery.

8. A method as in claim 1, wherein the first and second locations are extravascular.

9. A method of mapping baroreflex responsiveness, comprising the steps of:

provding an activation device;

positioning the activation device proximate a baroreceptor at a plurality of locations;

activating, deactivating or otherwise modulating the activation device at each location;

measuring the degree of baroreflex activation at each location; and comparing the degree of baroreflex activation at each location.

10. A method as in claim 9, wherein the step of measuring the degree of baroreflex activation comprises measuring blood pressure.

11. A method as in claim 9, wherein the step of measuring the degree of baroreflex activation comprises measuring heart rate.

12. A method as in claim 9, wherein the plurality of locations are on the same artery.

13. A method as in claim 9, wherein the plurality of locations are not all on the same artery.

14. A method as in claim 9, wherein the plurality of locations are extravascular.

15. A method of inducing a change in the baroreflex system of a patient, the method comprising the steps of:

providing an activation device;

selecting a location proximate a baroreceptor for implantation based on a comparison of baroreflex responsiveness;

positioning the activation device proximate a baroreceptor at the selected location; and activating, deactivating or otherwise modulating the activation device to induce a baroreceptor signal.

* * * * *